United States Patent
Liu et al.

(10) Patent No.: US 12,091,715 B2
(45) Date of Patent: Sep. 17, 2024

(54) METHODS AND COMPOSITIONS FOR REDUCING BASE ERRORS OF MASSIVE PARALLEL SEQUENCING USING TRISEQ SEQUENCING

(71) Applicant: Paragon Genomics, Inc., Fremont, CA (US)

(72) Inventors: Zhitong Liu, Foster City, CA (US);
David Debruyne, Hayward, CA (US);
Jack Dong, San Ramon, CA (US);
Michael Clark, Pleasanton, CA (US);
Yutao Fu, San Marcos, CA (US);
Vidushi Kapoor, Fremont, CA (US);
Kalyani Patankar, Wheeling, IL (US);
Fang Xie, San Francisco, CA (US);
Logan Tom, Alameda, CA (US)

(73) Assignee: Paragon Genomics, Inc., Fremont, CA (US)

( * ) Notice: Subject to any disclaimer, the term of this patent is extended or adjusted under 35 U.S.C. 154(b) by 0 days.

(21) Appl. No.: 18/180,843

(22) Filed: Mar. 8, 2023

(65) Prior Publication Data
US 2023/0340588 A1    Oct. 26, 2023

Related U.S. Application Data

(63) Continuation-in-part of application No. 17/726,480, filed on Apr. 21, 2022, now Pat. No. 11,680,293.

(51) Int. Cl.
| C12Q 1/6869 | (2018.01) |
| C12N 15/10 | (2006.01) |
| C12Q 1/6806 | (2018.01) |
| C12Q 1/6855 | (2018.01) |

(52) U.S. Cl.
CPC ....... *C12Q 1/6869* (2013.01); *C12N 15/1065* (2013.01); *C12Q 1/6806* (2013.01); *C12Q 1/6855* (2013.01); *C12Q 2600/16* (2013.01)

(58) Field of Classification Search
CPC .. C12Q 1/6869; C12Q 1/6806; C12Q 1/6855; C12Q 2600/16; C12Q 2563/179; C12Q 2525/191; C12N 15/1065
See application file for complete search history.

(56) References Cited

U.S. PATENT DOCUMENTS

| 4,683,195 A | 7/1987 | Mullis et al. |
| 4,683,202 A | 7/1987 | Mullis |
| 4,965,188 A | 10/1990 | Mullis et al. |
| 5,168,038 A | 12/1992 | Tecott et al. |
| 5,210,015 A | 5/1993 | Gelfand et al. |
| 5,399,491 A | 3/1995 | Kacian et al. |
| 5,539,082 A | 7/1996 | Nielsen et al. |
| 5,750,341 A | 5/1998 | Macevicz |
| 5,854,033 A | 12/1998 | Lizardi |
| 5,925,517 A | 7/1999 | Tyagi et al. |
| 6,174,670 B1 | 1/2001 | Wittwer et al. |
| 6,670,461 B1 | 12/2003 | Wengel et al. |
| 8,586,310 B2 | 11/2013 | Mitra et al. |
| 8,673,560 B2 | 3/2014 | Leamon et al. |
| 8,685,678 B2 | 4/2014 | Casbon et al. |
| 9,464,318 B2 | 10/2016 | Liu |
| 9,556,427 B2 | 1/2017 | Ji |
| 9,752,188 B2 | 9/2017 | Schmitt et al. |
| 10,100,358 B2 | 10/2018 | Liu et al. |
| 10,421,993 B2 | 9/2019 | Liu et al. |
| 10,941,453 B1 | 3/2021 | Liu et al. |
| 11,479,807 B2 | 10/2022 | Kennedy et al. |
| 2004/0185484 A1 | 9/2004 | Costa et al. |
| 2006/0234264 A1 | 10/2006 | Hardenbol |
| 2008/0014634 A1 | 1/2008 | Greener et al. |
| 2009/0123913 A1 | 5/2009 | Barany et al. |
| 2009/0203085 A1 | 8/2009 | Korn |

(Continued)

FOREIGN PATENT DOCUMENTS

| CN | 101575597 A | 11/2009 |
| JP | H04262799 A | 9/1992 |

(Continued)

OTHER PUBLICATIONS

Aboul-Maaty et al.; Extraction of high-quality genomic DNA from different plant orders applying a modified CTAB-based method; Bulletin of the National Research Centre; 43(1); 10 pages, doi 10.1186/s42269-019-0066-1; Dec. 2019.

Allawi et al.; Thermodynamics and NMR of internal GO T mismatches in DNA; Biochemistry; 36(340); pp. 10581-10594; Aug. 1997.

Altschul et al.; Gapped blast and psi-blast: a new generation of protein database search programs; Nucleic Acids Research; 25(17); pp. 3389-3402; Sep. 1997.

(Continued)

*Primary Examiner* — Angela M. Bertagna
*Assistant Examiner* — Francesca Filippa Giammona
(74) *Attorney, Agent, or Firm* — Shay Glenn LLP

(57) ABSTRACT

Methods and compositions for making DNA libraries for massive parallel next generation sequencing (NGS), comprises two parts. These methods may be referred to as Triseq sequencing. The first part includes ligating a UMI adapter, amplifying the DNA fragments in the presence of dUTP, enriching the target molecules through primer extension by using a panel of both forward and reverse primers, and removing the dU-containing template DNA. The DNA molecules are organized to primary clones and subclones, labeled by the UMI on 5' and 3' end of the DNA fragments, respectively. The second part includes sequencing the DNA library by NGS, deducing consensus sequence from each subclone, and from within each primary clone, and between the consensus sequences obtained from both forward and reverse primers.

18 Claims, 8 Drawing Sheets
Specification includes a Sequence Listing.

(56) References Cited

U.S. PATENT DOCUMENTS

| | | | |
|---|---|---|---|
| 2013/0261027 | A1 | 10/2013 | Li et al. |
| 2014/0227705 | A1 | 8/2014 | Vogelstein et al. |
| 2014/0322716 | A1 | 10/2014 | Robins |
| 2014/0329245 | A1 | 11/2014 | Spier et al. |
| 2014/0357500 | A1 | 12/2014 | Vigneault et al. |
| 2014/0378317 | A1 | 12/2014 | Fu et al. |
| 2015/0087027 | A1 | 3/2015 | Makarov et al. |
| 2016/0024493 | A1 | 1/2016 | Robins |
| 2016/0053253 | A1 | 2/2016 | Salathia et al. |
| 2016/0122753 | A1 | 5/2016 | Mikkelsen et al. |
| 2016/0312276 | A1 | 10/2016 | Fu et al. |
| 2017/0114406 | A1 | 4/2017 | Hansen et al. |
| 2017/0226498 | A1 | 8/2017 | Zheng et al. |
| 2018/0010176 | A1 | 1/2018 | Patel |
| 2018/0030515 | A1 | 2/2018 | Regev et al. |
| 2018/0163201 | A1 | 6/2018 | Larson |
| 2018/0340216 | A1* | 11/2018 | Jarosz ............... C12Q 1/6855 |
| 2019/0010489 | A1 | 1/2019 | Chang et al. |
| 2019/0112648 | A1 | 4/2019 | Schaal et al. |
| 2020/0109437 | A1 | 4/2020 | Chang et al. |
| 2020/0156071 | A1 | 5/2020 | Hansen et al. |
| 2020/0208143 | A1 | 7/2020 | Liu et al. |
| 2020/0248175 | A1* | 8/2020 | van Galen ........... C12Q 1/6881 |
| 2020/0256861 | A1 | 8/2020 | Johnston et al. |
| 2021/0180051 | A1 | 6/2021 | Liu et al. |
| 2021/0277461 | A1 | 9/2021 | Glezer et al. |
| 2021/0363517 | A1 | 11/2021 | Liu et al. |
| 2022/0220543 | A1 | 7/2022 | Salk |

FOREIGN PATENT DOCUMENTS

| | | | |
|---|---|---|---|
| WO | WO2005/095605 | A1 | 10/2005 |
| WO | WO2006/127423 | A2 | 11/2006 |
| WO | WO2006/138444 | A2 | 12/2006 |
| WO | WO2008/061193 | A2 | 5/2008 |
| WO | WO2012/149438 | A1 | 11/2012 |
| WO | WO2015/063154 | A1 | 5/2015 |
| WO | WO2016/040901 | A1 | 3/2016 |
| WO | WO2016/170147 | A1 | 10/2016 |

OTHER PUBLICATIONS

Anderson et al.; Protocol: a versatile, inexpensive, high-throughput plant genomic DNA extraction method suitable for genotyping-by-sequencing: Plant Methods: 14(1): 10 pages, doi.org/10.1186/s13007-018-0336-1; Dec. 2018.

Babon et al.; The use of resolvases T4 endonuclease VII and T7 endonuclease I in mutation detection; in Methods in Molecular Biology; vol. 152: DNA Repair Protocols: Prokaryotic systems; Edited by P. Vaughan; @ Humana Press Inc .; Totowa, NJ; pp. 187-199; Jul. 2000.

Bernard et al.; Color multiplexing hybridization probes using the apolipoprotein E locus as a model system for genotyping; Anal. Biochem .; 273(2); pp. 221-228; Sep. 10, 1999.

Casbon et al.; A method for counting PCR template molecules with application to next-generation sequencing; Nucleic Acids Res.; 39(12); 8 pages; e81.doi: 10.1093/nar/gkr217; Jul. 2011.

Chen et al.; Generation and analysis of a barcode-tagged insertion mutant library in the fission yeast schizosaccharomyces pombe; BMC Genomics; 13(1); 18 pages; retrieved from the internet (http://www.biomedcentral.com/1471-2164/13/161; Dec. 2012.

Crooke et al.; Section review biologicals and immunologicals: Progress in the development and patenting of antisense drug discovery technology; Expert Opinion on Therapeutic Patents; 6(9); pp. 855-870; Sep. 1, 1996.

Fu et al.; Counting individual DNA molecules by the stochastic attachment of diverse labels; Proc. Natl. Acad. Sci. USA; 108(22); pp. 9026-9031; May 31, 2011.

Fuhrmann et al; Removal of mismatched bases from synthetic genes by enzymatic mismatch cleavage; Nucleic Acids Research; 33(6); 8 pages; doi:10.1093/nar/gnl058; Jan. 2005.

Gregory et al; Targeted single molecule mutation detection with massively parallel sequencing; Nucleic Acids Res.; 44(3); 11 pages; e22. doi:10.1093/nar/gkv915; Feb. 18, 2016.

Hill-Ambroz et al.; Modified rapid DNA extraction protocol for high throughput microsatellite analysis in wheat; Crop Science; 42(6); pp. 2088-2091; 4 pages, doi: 10.2135/cropsci2002.2088; Nov. 2002.

Hoffmann et al.; DNA bar coding and pyrosequencing to identify rare HIV drug resistance mutations; Nucleic Acids Res.; 35(13); 8 pages; e91, doi:10.1093/nar/gkm435; ; Jun. 18, 2007.

Illumnia; Nextera XT Library Prep: Tips and Troubleshooting; retrieved from the internet (https://www.illumina.com/content/dam/illumina-marketing/documents/products/technotes/nextera-xt-troubleshooting-technical-note.pdf); 6 pages, on May 5, 2021.

Illumina; An introduction to next-generation sequencing technology; Illumina Inc; 2015; retrieved from the internet (https://www.illumina.com/content/dam/illumina-marketing/documents/products/illumina_sequencing_introduction.pdf) on Nov. 1, 2022.

Illumina; RNA sequencing methods; 122 pages; retrieved from the internet (https://www.illumina.com/content/dam/illumina-marketing/documents/products/research_reviews/ma-sequencing-methods-review-web.pdf) on Mar. 23, 2022.

Juvonen et al.; Amplification Facilitators and Pre-Processing Methods for PCR Detection of Strictly Anaerobic Beer-Spoilage Bacteria of the Class Clostridia in Brewery Samples; Journal of the Institute of Brewing and Distilling; 115(3); pp. 167-176; Aug. 1, 2009.

Kanehisa ; Use of statistical criteria for screening potential homologies in nucleic acid sequences; Nucleic Acids Res.; 12(1 prt 1); pp. 203-213; Jan. 11, 1984.

KASAJIMA; Successful tips of DNA extraction and PCR of plants for beginners; Trends in Research; 1(3): 1-2, 5 pages: doi: 10.15761/TR.1000115; Sep. 2018.

Kivioja et al.; Counting absolute numbers of molecules using unique molecular identifiers; Nat. Methods; 9(1); pp. 72-74; (Author Manuscript); Nov. 20, 2011.

Kohn et al.; Single-Cell Semiconductor Sequencing; Methods in Molecular Biology; Chapter 18; 148; pp. 247-284, 2017.

Leone et al; Molecular beacon probes combined with amplification by NASBA enable homogeneous, real-time detection of RNA; Nucleic Acids Res.; 26(9); pp. 2150-2155; May 1, 1998.

Li et al.; A universal method for direct PCR amplification of plant tissues; Analytical Methods; 9(11); pp. 1800-1805; 6 pages; doi: 10.1039/C6AY03156K; (the year of publication is sufficiently earlier than the effective U.S. filing date and any foreign priority date so that the particular month of publication is not in issue) 2017.

Lowell et al.; Heteroduplex resolution using T7 endonuclease I in microbial community analyses; Bio Techniques; 28(4); pp. 676-681; Apr. 2000.

Mackay et al.; Real-time PCR in virology; Nucleic Acids Research; 30(6); pp. 1292-1305; Mar. 15, 2002.

Mardis; The impact of next-generation sequencing technology on genetics; Trends in Genetics; 24(3); pp. 133-141; Mar. 1, 2008.

McDonough et al.; Use of FFPE-derived DNA in next generation sequencing: DNA extraction methods; Plos one; 14(4); 15 pages; doi: 10.1371/journal.pone.0211400; Apr. 2019.

Mesmaeker et al.; Backbone modifications in oligonucleotides and peptide nucleic acid systems; Current Opinion in Structural Biology; 5(3); pp. 343-355; Jun. 1995.

Needleman et al.; A general method applicable to the search for similarities in the amino acid sequence of two proteins; Journal of Molecular Biology; 48(3); pp. 443-453; May 1970.

Newman et al.; Integrated digital error suppression for improved detection of circulating tumor DNA; Nature Biotechnology; 34(5); pp. 547-555, doi: 10.1038/nbt.3520; (Author Manuscript); May 2016.

Phallen et al.; Direct detection of early-stage cancers using circulating tumor DNA; Sci. Transl. Med.; 9(403); pii: eaan2415. doi: 10.1126/scritranslmed.aan2415; Aug. 16, 2017.

Qiu et al.; Evaluation of PCR-generated chimeras, mutations, and heteroduplexes with 16S rRNA gene-based cloning. Applied and Environmental Microbiology. 67(2): pp. 880-887; Feb. 1, 2001.

(56) References Cited

OTHER PUBLICATIONS

Rana et al.; Optimized nuclear pellet method for extracting next-generation sequencing quality genomic DNA from fresh leaf tissue; Methods and protocols; 2(2):54; 11 pages, doi: 10.3390/mps2020054; ; Jun. 2019.
Schmitt et al.; Detection of ultra-rare mutations by next-generation sequencing; Proc. Natl. Acad. Sci. USA; 109(36); pp. 14508-14513; Sep. 4, 2012.
Shendure et al.; Next-generation DNA sequencing; Nature Biotechnology; 26(10); pp. 1135-1145; Oct. 2008.
Smith et al.; Comparison of biosequences; Advances in Applied Mathematics; 2(4); pp. 482-489; Dec. 1981.
Stahlberg et al.; Simple, multiplexed, PCR-based barcoding of DNA enables sensitive mutation detection in liquid biopsies using sequencing; Nucleic Acids Res.; 44(11); pp. 1-7; e105. doi: 10.1093/nar/gkw224; Jun. 20, 2016.
Stoler et al.; Streamlined analysis of duplex sequencing data with du novo; Genome Biology; 17(1); 10 pages; DOI 10.1186/s13059-016-1039-4; Dec. 2016.
Su et al.; Next-generation sequencing and its applications in molecular diagnostics; Expert Rev. Mol. Diagn.; 11(3); pp. 333-343; Apr. 2011.
Takishita et al.; Genetic diversity of microbial eukaryotes in anoxic sediment of the saline meromictic lake namako-ike (japan): on the detection of anaerobic or anoxic-tolerant lineages of eukaryotes; Protist; 158(1); pp. 51-64; Jan. 2007.
Tan et al.; DNA, RNA, and protein extraction: the past and the present: Journal of Biomedicine and Biotechnology; Hindawi Publishing Corporation; 10 pages, doi:10.1155/2009/574398; Nov. 2009.
Uhlman et al.; Antisense oligonucleotides: a new therapeutic principle; Chemical Reviews; 90(4); pp. 543-584; Jun. 1, 1990.
Von Post et al.; A high-throughput DNA extraction method for barley seed; Euphytica; 130(2); pp. 255-260; 6 pages, doi 10.1023/A:1022863006134; Mar. 2003.
Wang et al.; A rapid and cheap protocol for preparation of PCR templates in peanut: Electronic Journal of Biotechnology; 12(2); pp. 9-10; 7 pages, doi 10.2225/vol12-issue2-fulltext-11; Apr. 2009.
Wang et al.; A simple method of preparing plant samples for PCR; Nucleic Acids Research; 21(17); pp. 4153-4154; Aug. 1993.
Wang et al.; Targeted sequencing of both DNA strands barcoded and captured individually by RNA probes to identify genome-wide ultra-rare mutations; Scientific Reports; 7(1); 14 pages; 3356 DOI:10.1038/s41598-017-03448-8; Jun. 13, 2017.
Wang et al., Use of template switching oligos (TS oligos, TSOs) for efficient cDNA library construction; 4 pages; retrieved from the internet (https://www.idtdna.com/pages/education/decoded/article/use-of-template-switching-oligos-(ts-cligos-tsos)-for-efficient-cdna-library-construction) on Mar. 23, 2022.
Werner et al.; Direct amplification and NaOH extraction: two rapid and simple methods for preparing bryophyte DNA for polymerase chain reaction (PCR); Journal of Bryology; 24(2); pp. 127-131; 5 pages, doi: 10.1179/037366802125000980; Jun. 2002.
Young et al.; Efficient isolation of genes by using antibody probes; Proc. Natl. Acad. Sci.USA; 80(5); pp. 1194-1198; Mar. 1983.
Zhang et al.; Elimination of primer—dimer effect in SYBR green I real--time RT--PCR using 4--step program. Chinese Journal of Biochemistry and Molecular Biology; 2004; 20(3); pp. 387-392; (Machine Translated English Abstract); Dec. 31, 2003.
Zhang et al.; The impact of next-generation sequencing on genomics; J. Genet. Genomics; 38(3); pp. 95-109; (Author Manuscript) Mar. 20, 2011.
Lin et al.; A convenient method to remove primer dimer in polymerase chain reaction; Journal of Xinxiang Medical College: 29(6); pp. 617-418, 421; (Machine Translated English Abstract); Jun. 5, 2012.
Liu et al.; U.S. Appl. No. 16/741,272 entitled "Methods and compositions for preparation of crude lysate of nucleic acids," filed Jan. 13, 2020.
Liu et al.; U.S. Appl. No. 17/726,480 entitled "Methods and compositions for amplifying dna and generating dna sequencing results from target-enriched dna molecules," filed Apr. 21, 2022.

\* cited by examiner

SEQUENCE LISTING

```
Sequence total quantity: 89
SEQ ID NO: 1                    moltype = DNA   length = 39
FEATURE                         Location/Qualifiers
source                          1..39
                                mol_type = other DNA
                                organism = synthetic construct
misc_feature                    36..39
                                note = RNA
misc_feature                    1..35
                                note = DNA
SEQUENCE: 1
cctacacgac gctcttccga tctnnnnnnn nnnnnnnnn                            39

SEQ ID NO: 2                    moltype = DNA   length = 86
FEATURE                         Location/Qualifiers
source                          1..86
                                mol_type = other DNA
                                organism = synthetic construct
misc_feature                    83..86
                                note = RNA
misc_feature                    1..82
                                note = DNA
SEQUENCE: 2
aatgatacgg cgaccaccga gatctacacn nnnnnnaca ctctttccct acacgacgct      60
cttccgatct nnnnnnnnnn nnnnnn                                          86

SEQ ID NO: 3                    moltype = DNA   length = 23
FEATURE                         Location/Qualifiers
source                          1..23
                                mol_type = other DNA
                                organism = synthetic construct
modified_base                   order(13,16,21)
                                mod_base = OTHER
                                note = Internal deoxy Uracil
SEQUENCE: 3
cctacacgac gctcttccga tct                                             23

SEQ ID NO: 4                    moltype = DNA   length = 70
FEATURE                         Location/Qualifiers
source                          1..70
                                mol_type = other DNA
                                organism = synthetic construct
modified_base                   69^70
                                mod_base = OTHER
                                note = Phosphorothioate linkage
SEQUENCE: 4
aatgatacgg cgaccaccga gatctacacn nnnnnnaca ctctttccct acacgacgct      60
cttccgatct                                                            70

SEQ ID NO: 5                    moltype = DNA   length = 66
FEATURE                         Location/Qualifiers
source                          1..66
                                mol_type = other DNA
                                organism = synthetic construct
modified_base                   65^66
                                mod_base = OTHER
                                note = Phosphorothioate linkage
SEQUENCE: 5
caagcagaag acggcatacg agatnnnnnn nngtgactgg agttcagacg tgtgctcttc     60
cgatct                                                                66

SEQ ID NO: 6                    moltype = DNA   length = 46
FEATURE                         Location/Qualifiers
source                          1..46
                                mol_type = other DNA
                                organism = synthetic construct
SEQUENCE: 6
ttcagacgtg tgctcttccg atctnnncag tctacctccc gccata                    46

SEQ ID NO: 7                    moltype = DNA   length = 54
FEATURE                         Location/Qualifiers
source                          1..54
                                mol_type = other DNA
                                organism = synthetic construct
SEQUENCE: 7
ttcagacgtg tgctcttccg atctnnncag accagctttc aaaaagaaaa ttgt           54

SEQ ID NO: 8                    moltype = DNA   length = 50
```

```
FEATURE              Location/Qualifiers
source               1..50
                     mol_type = other DNA
                     organism = synthetic construct
SEQUENCE: 8
ttcagacgtg tgctcttccg atctnnncaa agaagaaacc actggatgga          50

SEQ ID NO: 9         moltype = DNA   length = 44
FEATURE              Location/Qualifiers
source               1..44
                     mol_type = other DNA
                     organism = synthetic construct
SEQUENCE: 9
ttcagacgtg tgctcttccg atctnnnccc ccagggagca ctaa                44

SEQ ID NO: 10        moltype = DNA   length = 46
FEATURE              Location/Qualifiers
source               1..46
                     mol_type = other DNA
                     organism = synthetic construct
SEQUENCE: 10
ttcagacgtg tgctcttccg atctnnnacg gaacagcttt gaggtg              46

SEQ ID NO: 11        moltype = DNA   length = 48
FEATURE              Location/Qualifiers
source               1..48
                     mol_type = other DNA
                     organism = synthetic construct
SEQUENCE: 11
ttcagacgtg tgctcttccg atctnnngcc tcttgcttct cttttcct            48

SEQ ID NO: 12        moltype = DNA   length = 51
FEATURE              Location/Qualifiers
source               1..51
                     mol_type = other DNA
                     organism = synthetic construct
SEQUENCE: 12
ttcagacgtg tgctcttccg atctnnngac aggtaggacc tgatttcctt a        51

SEQ ID NO: 13        moltype = DNA   length = 47
FEATURE              Location/Qualifiers
source               1..47
                     mol_type = other DNA
                     organism = synthetic construct
SEQUENCE: 13
ttcagacgtg tgctcttccg atctnnntga ctgtaccacc atccact             47

SEQ ID NO: 14        moltype = DNA   length = 47
FEATURE              Location/Qualifiers
source               1..47
                     mol_type = other DNA
                     organism = synthetic construct
SEQUENCE: 14
ttcagacgtg tgctcttccg atctnnnata gtgtggtggt gccctat             47

SEQ ID NO: 15        moltype = DNA   length = 46
FEATURE              Location/Qualifiers
source               1..46
                     mol_type = other DNA
                     organism = synthetic construct
SEQUENCE: 15
ttcagacgtg tgctcttccg atctnnntca ctgaagaccc aggtcc              46

SEQ ID NO: 16        moltype = DNA   length = 51
FEATURE              Location/Qualifiers
source               1..51
                     mol_type = other DNA
                     organism = synthetic construct
SEQUENCE: 16
ttcagacgtg tgctcttccg atctnnntga aaacaacgtt ctggtaagga c        51

SEQ ID NO: 17        moltype = DNA   length = 50
FEATURE              Location/Qualifiers
source               1..50
                     mol_type = other DNA
                     organism = synthetic construct
SEQUENCE: 17
ttcagacgtg tgctcttccg atctnnncct atggaaactg tgagtggatc          50
```

```
SEQ ID NO: 18            moltype = DNA   length = 47
FEATURE                  Location/Qualifiers
source                   1..47
                         mol_type = other DNA
                         organism = synthetic construct
SEQUENCE: 18
ttcagacgtg tgctcttccg atctnnntgg aagtgtctca tgctgga            47

SEQ ID NO: 19            moltype = DNA   length = 52
FEATURE                  Location/Qualifiers
source                   1..52
                         mol_type = other DNA
                         organism = synthetic construct
SEQUENCE: 19
ttcagacgtg tgctcttccg atctnnnaaa aactcatgtt caagacagaa gg       52

SEQ ID NO: 20            moltype = DNA   length = 51
FEATURE                  Location/Qualifiers
source                   1..51
                         mol_type = other DNA
                         organism = synthetic construct
SEQUENCE: 20
ttcagacgtg tgctcttccg atctnnntca ctcatgtgat gtcatctctc c        51

SEQ ID NO: 21            moltype = DNA   length = 49
FEATURE                  Location/Qualifiers
source                   1..49
                         mol_type = other DNA
                         organism = synthetic construct
SEQUENCE: 21
ttcagacgtg tgctcttccg atctnnngaa tgaggccttg gaactcaag           49

SEQ ID NO: 22            moltype = DNA   length = 53
FEATURE                  Location/Qualifiers
source                   1..53
                         mol_type = other DNA
                         organism = synthetic construct
SEQUENCE: 22
ttcagacgtg tgctcttccg atctnnntgt atatacttac ttctcccct cct       53

SEQ ID NO: 23            moltype = DNA   length = 52
FEATURE                  Location/Qualifiers
source                   1..52
                         mol_type = other DNA
                         organism = synthetic construct
SEQUENCE: 23
ttcagacgtg tgctcttccg atctnnnggt tctatgactt tgcctgatac ag       52

SEQ ID NO: 24            moltype = DNA   length = 57
FEATURE                  Location/Qualifiers
source                   1..57
                         mol_type = other DNA
                         organism = synthetic construct
SEQUENCE: 24
ttcagacgtg tgctcttccg atctnnngaa aattgttaaa gagagcatga aaatggt  57

SEQ ID NO: 25            moltype = DNA   length = 52
FEATURE                  Location/Qualifiers
source                   1..52
                         mol_type = other DNA
                         organism = synthetic construct
SEQUENCE: 25
ttcagacgtg tgctcttccg atctnnncct ggttgtagct aactaacttc ag       52

SEQ ID NO: 26            moltype = DNA   length = 52
FEATURE                  Location/Qualifiers
source                   1..52
                         mol_type = other DNA
                         organism = synthetic construct
SEQUENCE: 26
ttcagacgtg tgctcttccg atctnnnctt ttatcacctt tccttgcctc tt       52

SEQ ID NO: 27            moltype = DNA   length = 51
FEATURE                  Location/Qualifiers
source                   1..51
                         mol_type = other DNA
                         organism = synthetic construct
SEQUENCE: 27
ttcagacgtg tgctcttccg atctnnngca gttatgcctc agattcactt t        51
```

```
SEQ ID NO: 28            moltype = DNA  length = 50
FEATURE                  Location/Qualifiers
source                   1..50
                         mol_type = other DNA
                         organism = synthetic construct
SEQUENCE: 28
ttcagacgtg tgctcttccg atctnnngga agagaatctc cgcaagaaag              50

SEQ ID NO: 29            moltype = DNA  length = 48
FEATURE                  Location/Qualifiers
source                   1..48
                         mol_type = other DNA
                         organism = synthetic construct
SEQUENCE: 29
ttcagacgtg tgctcttccg atctnnngtg gtaatctact gggacgga                48

SEQ ID NO: 30            moltype = DNA  length = 47
FEATURE                  Location/Qualifiers
source                   1..47
                         mol_type = other DNA
                         organism = synthetic construct
SEQUENCE: 30
ttcagacgtg tgctcttccg atctnnngga gtagatggag cctggtt                 47

SEQ ID NO: 31            moltype = DNA  length = 49
FEATURE                  Location/Qualifiers
source                   1..49
                         mol_type = other DNA
                         organism = synthetic construct
SEQUENCE: 31
ttcagacgtg tgctcttccg atctnnncca tcatcacact ggaagactc               49

SEQ ID NO: 32            moltype = DNA  length = 44
FEATURE                  Location/Qualifiers
source                   1..44
                         mol_type = other DNA
                         organism = synthetic construct
SEQUENCE: 32
ttcagacgtg tgctcttccg atctnnnatg ggcggcatga accg                    44

SEQ ID NO: 33            moltype = DNA  length = 48
FEATURE                  Location/Qualifiers
source                   1..48
                         mol_type = other DNA
                         organism = synthetic construct
SEQUENCE: 33
ttcagacgtg tgctcttccg atctnnncct catcttgggc ctgtgtta                48

SEQ ID NO: 34            moltype = DNA  length = 48
FEATURE                  Location/Qualifiers
source                   1..48
                         mol_type = other DNA
                         organism = synthetic construct
SEQUENCE: 34
ttcagacgtg tgctcttccg atctnnnaag gaaatttgcg tgtggagt                48

SEQ ID NO: 35            moltype = DNA  length = 49
FEATURE                  Location/Qualifiers
source                   1..49
                         mol_type = other DNA
                         organism = synthetic construct
SEQUENCE: 35
ttcagacgtg tgctcttccg atctnnncac tgattgctct taggtctgg               49

SEQ ID NO: 36            moltype = DNA  length = 46
FEATURE                  Location/Qualifiers
source                   1..46
                         mol_type = other DNA
                         organism = synthetic construct
SEQUENCE: 36
ttcagacgtg tgctcttccg atctnnncgc tgctcagata gcgatg                  46

SEQ ID NO: 37            moltype = DNA  length = 46
FEATURE                  Location/Qualifiers
source                   1..46
                         mol_type = other DNA
                         organism = synthetic construct
SEQUENCE: 37
```

```
ttcagacgtg tgctcttccg atctnnncgc catggccatc tacaag        46

SEQ ID NO: 38           moltype = DNA   length = 49
FEATURE                 Location/Qualifiers
source                  1..49
                        mol_type = other DNA
                        organism = synthetic construct
SEQUENCE: 38
ttcagacgtg tgctcttccg atctnnncct gccctcaaca agatgttttt     49

SEQ ID NO: 39           moltype = DNA   length = 49
FEATURE                 Location/Qualifiers
source                  1..49
                        mol_type = other DNA
                        organism = synthetic construct
SEQUENCE: 39
ttcagacgtg tgctcttccg atctnnnccc tgactttcaa ctctgtctc      49

SEQ ID NO: 40           moltype = DNA   length = 46
FEATURE                 Location/Qualifiers
source                  1..46
                        mol_type = other DNA
                        organism = synthetic construct
SEQUENCE: 40
ttcagacgtg tgctcttccg atctnnntga cttgcacggt cagttg         46

SEQ ID NO: 41           moltype = DNA   length = 48
FEATURE                 Location/Qualifiers
source                  1..48
                        mol_type = other DNA
                        organism = synthetic construct
SEQUENCE: 41
ttcagacgtg tgctcttccg atctnnngtc ccttcccaga aaacctac       48

SEQ ID NO: 42           moltype = DNA   length = 48
FEATURE                 Location/Qualifiers
source                  1..48
                        mol_type = other DNA
                        organism = synthetic construct
SEQUENCE: 42
ttcagacgtg tgctcttccg atctnnncag atgaagctcc cagaatgc       48

SEQ ID NO: 43           moltype = DNA   length = 47
FEATURE                 Location/Qualifiers
source                  1..47
                        mol_type = other DNA
                        organism = synthetic construct
SEQUENCE: 43
ttcagacgtg tgctcttccg atctnnngtc cccggacgat attgaac        47

SEQ ID NO: 44           moltype = DNA   length = 48
FEATURE                 Location/Qualifiers
source                  1..48
                        mol_type = other DNA
                        organism = synthetic construct
SEQUENCE: 44
ttcagacgtg tgctcttccg atctnnntgg tcctctgact gctctttt       48

SEQ ID NO: 45           moltype = DNA   length = 46
FEATURE                 Location/Qualifiers
source                  1..46
                        mol_type = other DNA
                        organism = synthetic construct
SEQUENCE: 45
ttcagacgtg tgctcttccg atctnnnccc ctagcagaga cctgtg         46

SEQ ID NO: 46           moltype = DNA   length = 46
FEATURE                 Location/Qualifiers
source                  1..46
                        mol_type = other DNA
                        organism = synthetic construct
SEQUENCE: 46
ttcagacgtg tgctcttccg atctnnnagc cgcagtcaga tcctag         46

SEQ ID NO: 47           moltype = DNA   length = 48
FEATURE                 Location/Qualifiers
source                  1..48
                        mol_type = other DNA
                        organism = synthetic construct
```

```
SEQUENCE: 47
ttcagacgtg tgctcttccg atctnnncca cttttcctct tgcagcag                48

SEQ ID NO: 48           moltype = DNA  length = 52
FEATURE                 Location/Qualifiers
source                  1..52
                        mol_type = other DNA
                        organism = synthetic construct
SEQUENCE: 48
ttcagacgtg tgctcttccg atctnnngtt caaagaccca aaacccaaaa tg           52

SEQ ID NO: 49           moltype = DNA  length = 50
FEATURE                 Location/Qualifiers
source                  1..50
                        mol_type = other DNA
                        organism = synthetic construct
SEQUENCE: 49
ttcagacgtg tgctcttccg atctnnntgg agaatgtcag tctgagtcag              50

SEQ ID NO: 50           moltype = DNA  length = 50
FEATURE                 Location/Qualifiers
source                  1..50
                        mol_type = other DNA
                        organism = synthetic construct
SEQUENCE: 50
ttcagacgtg tgctcttccg atctnnncct atggctttcc aacctaggaa              50

SEQ ID NO: 51           moltype = DNA  length = 47
FEATURE                 Location/Qualifiers
source                  1..47
                        mol_type = other DNA
                        organism = synthetic construct
SEQUENCE: 51
ttcagacgtg tgctcttccg atctnnnggt cactcacctg gagtgag                 47

SEQ ID NO: 52           moltype = DNA  length = 54
FEATURE                 Location/Qualifiers
source                  1..54
                        mol_type = other DNA
                        organism = synthetic construct
SEQUENCE: 52
ttcagacgtg tgctcttccg atctnnnagg ctaagctatg atgttcctta gatt         54

SEQ ID NO: 53           moltype = DNA  length = 57
FEATURE                 Location/Qualifiers
source                  1..57
                        mol_type = other DNA
                        organism = synthetic construct
SEQUENCE: 53
ttcagacgtg tgctcttccg atctnnnaac ttacaatatt ttcaacttac gacgagt      57

SEQ ID NO: 54           moltype = DNA  length = 54
FEATURE                 Location/Qualifiers
source                  1..54
                        mol_type = other DNA
                        organism = synthetic construct
SEQUENCE: 54
ttcagacgtg tgctcttccg atctnnngca aagtcataga accattttca tgct         54

SEQ ID NO: 55           moltype = DNA  length = 53
FEATURE                 Location/Qualifiers
source                  1..53
                        mol_type = other DNA
                        organism = synthetic construct
SEQUENCE: 55
ttcagacgtg tgctcttccg atctnnngga aactttccac ttgataagag gtc          53

SEQ ID NO: 56           moltype = DNA  length = 52
FEATURE                 Location/Qualifiers
source                  1..52
                        mol_type = other DNA
                        organism = synthetic construct
SEQUENCE: 56
ttcagacgtg tgctcttccg atctnnntga agggtgaaat attctccatc ca           52

SEQ ID NO: 57           moltype = DNA  length = 53
FEATURE                 Location/Qualifiers
source                  1..53
                        mol_type = other DNA
```

```
                              organism = synthetic construct
SEQUENCE: 57
ttcagacgtg tgctcttccg atctnnntaa aagtgaatct gaggcataac tgc         53

SEQ ID NO: 58           moltype = DNA  length = 47
FEATURE                 Location/Qualifiers
source                  1..47
                        mol_type = other DNA
                        organism = synthetic construct
SEQUENCE: 58
ttcagacgtg tgctcttccg atctnnntgc ttacctcgct tagtgct                47

SEQ ID NO: 59           moltype = DNA  length = 46
FEATURE                 Location/Qualifiers
source                  1..46
                        mol_type = other DNA
                        organism = synthetic construct
SEQUENCE: 59
ttcagacgtg tgctcttccg atctnnngca caaacacgca cctcaa                 46

SEQ ID NO: 60           moltype = DNA  length = 50
FEATURE                 Location/Qualifiers
source                  1..50
                        mol_type = other DNA
                        organism = synthetic construct
SEQUENCE: 60
ttcagacgtg tgctcttccg atctnnngag gtggatgggt agtagtatgg             50

SEQ ID NO: 61           moltype = DNA  length = 49
FEATURE                 Location/Qualifiers
source                  1..49
                        mol_type = other DNA
                        organism = synthetic construct
SEQUENCE: 61
ttcagacgtg tgctcttccg atctnnngga agaaatcggt aagaggtgg              49

SEQ ID NO: 62           moltype = DNA  length = 49
FEATURE                 Location/Qualifiers
source                  1..49
                        mol_type = other DNA
                        organism = synthetic construct
SEQUENCE: 62
ttcagacgtg tgctcttccg atctnnncca gtgtgatgat ggtgaggat              49

SEQ ID NO: 63           moltype = DNA  length = 48
FEATURE                 Location/Qualifiers
source                  1..48
                        mol_type = other DNA
                        organism = synthetic construct
SEQUENCE: 63
ttcagacgtg tgctcttccg atctnnncca ctgacaacca cccttaac               48

SEQ ID NO: 64           moltype = DNA  length = 47
FEATURE                 Location/Qualifiers
source                  1..47
                        mol_type = other DNA
                        organism = synthetic construct
SEQUENCE: 64
ttcagacgtg tgctcttccg atctnnnata gggcaccacc acactat                47

SEQ ID NO: 65           moltype = DNA  length = 49
FEATURE                 Location/Qualifiers
source                  1..49
                        mol_type = other DNA
                        organism = synthetic construct
SEQUENCE: 65
ttcagacgtg tgctcttccg atctnnnttc cactcggata agatgctga              49

SEQ ID NO: 66           moltype = DNA  length = 44
FEATURE                 Location/Qualifiers
source                  1..44
                        mol_type = other DNA
                        organism = synthetic construct
SEQUENCE: 66
ttcagacgtg tgctcttccg atctnnngca accagccctg tcgt                   44

SEQ ID NO: 67           moltype = DNA  length = 46
FEATURE                 Location/Qualifiers
source                  1..46
```

```
                              mol_type = other DNA
                              organism = synthetic construct
SEQUENCE: 67
ttcagacgtg tgctcttccg atctnnnctc acaacctccg tcatgt              46

SEQ ID NO: 68                 moltype = DNA   length = 46
FEATURE                       Location/Qualifiers
source                        1..46
                              mol_type = other DNA
                              organism = synthetic construct
SEQUENCE: 68
ttcagacgtg tgctcttccg atctnnnggg tgtggaatca acccac              46

SEQ ID NO: 69                 moltype = DNA   length = 50
FEATURE                       Location/Qualifiers
source                        1..50
                              mol_type = other DNA
                              organism = synthetic construct
SEQUENCE: 69
ttcagacgtg tgctcttccg atctnnnggt gaagaggaat cccaaagttc          50

SEQ ID NO: 70                 moltype = DNA   length = 49
FEATURE                       Location/Qualifiers
source                        1..49
                              mol_type = other DNA
                              organism = synthetic construct
SEQUENCE: 70
ttcagacgtg tgctcttccg atctnnncat tgaagtctca tggaagcca           49

SEQ ID NO: 71                 moltype = DNA   length = 45
FEATURE                       Location/Qualifiers
source                        1..45
                              mol_type = other DNA
                              organism = synthetic construct
SEQUENCE: 71
ttcagacgtg tgctcttccg atctnnncag acggaaaccg tagct               45

SEQ ID NO: 72                 moltype = DNA   length = 47
FEATURE                       Location/Qualifiers
source                        1..47
                              mol_type = other DNA
                              organism = synthetic construct
SEQUENCE: 72
ttcagacgtg tgctcttccg atctnnnagg gacagaagat gacaggg             47

SEQ ID NO: 73                 moltype = DNA   length = 46
FEATURE                       Location/Qualifiers
source                        1..46
                              mol_type = other DNA
                              organism = synthetic construct
SEQUENCE: 73
ttcagacgtg tgctcttccg atctnnnctg gacctgggtc ttcagt              46

SEQ ID NO: 74                 moltype = DNA   length = 46
FEATURE                       Location/Qualifiers
source                        1..46
                              mol_type = other DNA
                              organism = synthetic construct
SEQUENCE: 74
ttcagacgtg tgctcttccg atctnnnagc ccaacccttg tcctta              46

SEQ ID NO: 75                 moltype = DNA   length = 48
FEATURE                       Location/Qualifiers
source                        1..48
                              mol_type = other DNA
                              organism = synthetic construct
SEQUENCE: 75
ttcagacgtg tgctcttccg atctnnntgg aattttcgct tcccacag            48

SEQ ID NO: 76                 moltype = DNA   length = 54
FEATURE                       Location/Qualifiers
source                        1..54
                              mol_type = other DNA
                              organism = synthetic construct
SEQUENCE: 76
ttcagacgtg tgctcttccg atctnnnaca gtttccatag gtctgaaaat gttt     54

SEQ ID NO: 77                 moltype = DNA   length = 47
FEATURE                       Location/Qualifiers
```

```
source                          1..47
                                mol_type = other DNA
                                organism = synthetic construct
SEQUENCE: 77
ttcagacgtg tgctcttccg atctnnngac ccaaaaccca aaatggc            47

SEQ ID NO: 78                   moltype = DNA   length = 49
FEATURE                         Location/Qualifiers
source                          1..49
                                mol_type = other DNA
                                organism = synthetic construct
SEQUENCE: 78
ttcagacgtg tgctcttccg atctnnnctc attcagctct cggaacatc          49

SEQ ID NO: 79                   moltype = DNA   length = 52
FEATURE                         Location/Qualifiers
source                          1..52
                                mol_type = other DNA
                                organism = synthetic construct
SEQUENCE: 79
ttcagacgtg tgctcttccg atctnnngtt agactggaaa ctttccactt ga      52

SEQ ID NO: 80                   moltype = DNA   length = 45
FEATURE                         Location/Qualifiers
source                          1..45
                                mol_type = other DNA
                                organism = synthetic construct
SEQUENCE: 80
ttcagacgtg tgctcttccg atctnnnggg agaggagctg gtgtt              45

SEQ ID NO: 81                   moltype = DNA   length = 44
FEATURE                         Location/Qualifiers
source                          1..44
                                mol_type = other DNA
                                organism = synthetic construct
SEQUENCE: 81
ttcagacgtg tgctcttccg atctnnncag ctcgtggtga ggct               44

SEQ ID NO: 82                   moltype = DNA   length = 49
FEATURE                         Location/Qualifiers
source                          1..49
                                mol_type = other DNA
                                organism = synthetic construct
SEQUENCE: 82
ttcagacgtg tgctcttccg atctnnnccg tcccagtaga ttaccacta          49

SEQ ID NO: 83                   moltype = DNA   length = 44
FEATURE                         Location/Qualifiers
source                          1..44
                                mol_type = other DNA
                                organism = synthetic construct
SEQUENCE: 83
ttcagacgtg tgctcttccg atctnnncac agcaggccag tgtg               44

SEQ ID NO: 84                   moltype = DNA   length = 48
FEATURE                         Location/Qualifiers
source                          1..48
                                mol_type = other DNA
                                organism = synthetic construct
SEQUENCE: 84
ttcagacgtg tgctcttccg atctnnnccc atgcaggaac tgttacac           48

SEQ ID NO: 85                   moltype = DNA   length = 47
FEATURE                         Location/Qualifiers
source                          1..47
                                mol_type = other DNA
                                organism = synthetic construct
SEQUENCE: 85
ttcagacgtg tgctcttccg atctnnnagt tgcaaaccag acctcag            47

SEQ ID NO: 86                   moltype = DNA   length = 46
FEATURE                         Location/Qualifiers
source                          1..46
                                mol_type = other DNA
                                organism = synthetic construct
SEQUENCE: 86
ttcagacgtg tgctcttccg atctnnntag ctgccctggt aggttt             46

SEQ ID NO: 87                   moltype = DNA   length = 46
```

```
FEATURE            Location/Qualifiers
source             1..46
                   mol_type = other DNA
                   organism = synthetic construct
SEQUENCE: 87
ttcagacgtg tgctcttccg atctnnnggc attctgggag cttcat                46

SEQ ID NO: 88      moltype = DNA  length = 50
FEATURE            Location/Qualifiers
source             1..50
                   mol_type = other DNA
                   organism = synthetic construct
SEQUENCE: 88
ttcagacgtg tgctcttccg atctnnnatc aaatcatcca ttgcttggga            50

SEQ ID NO: 89      moltype = DNA  length = 46
FEATURE            Location/Qualifiers
source             1..46
                   mol_type = other DNA
                   organism = synthetic construct
SEQUENCE: 89
ttcagacgtg tgctcttccg atctnnncct gcccttccaa tggatc                46
```

METHODS AND COMPOSITIONS FOR REDUCING BASE ERRORS OF MASSIVE PARALLEL SEQUENCING USING TRISEQ SEQUENCING

CLAIM OF PRIORITY

This patent application claims priority as a continuation-in-part of U.S. patent application Ser. No. 17/726,480, titled "METHODS AND COMPOSITIONS FOR AMPLIFYING DNA AND GENERATING DNA SEQUENCING RESULTS FROM TARGET-ENRICHED DNA MOLECULES," filed on Apr. 21, 2022, now U.S. Pat. No. 11,680,293, and herein incorporated by reference in its entirety.

SEQUENCE LISTING

The instant application contains a Sequence Listing which has been filed electronically in ASCII format and is hereby incorporated by reference in its entirety. Said ASCII copy, created on May 8, 2024 is named 13982-706-500.txt and is 85,239 bytes in size.

INCORPORATION BY REFERENCE

All publications and patent applications mentioned in this specification are herein incorporated by reference in their entirety to the same extent as if each individual publication or patent application was specifically and individually indicated to be incorporated by reference, and for any purpose. When definitions of terms in incorporated references appear to differ from the definitions provided in the present teachings, the definition provided in the present teachings shall control.

BACKGROUND

Unique molecular identifiers (UMIs), or molecular barcodes, have been used widely in massive parallel sequencing (e.g., next generation sequencing, NGS) since its introduction in 2011, and helps improve the sensitivity of NGS while providing a quantitative tool for the measurement of mutations. The adoption of UMI in NGS ushers in an era of liquid biopsy. After ten years of development of various UMI technologies, UMI has been successfully used in liquid biopsy tests involving several types of cancers in advanced stages. However, many problems persist when UMI technology is used in testing early-stage cancers. The first major problem is that the detection of rare mutations (below 0.5% variant allele frequency) is unreliable and varies widely between assays, represented by the high levels of the false positives and false negatives. The second challenge is the sampling of rare ctDNA fragments. The root cause for these two major problems arises from the techniques used in making the libraries for liquid biopsy.

UMI, in the form of a stretch of random bases or degenerate nucleotides, was first used to label the target molecules through either PCR or ligation. Subsequently, many variations of both PCR- and ligation-based methods were developed. These include (but are not limited to) the PCR-based methods of TAM-seq, cTAM-seq, SAFE-SeqS, SiMSen-Seq, Kou 2016, AmpliSeq HD, and the ligation-based methods of Duplex-Seq, Tec-Seq, Kukita 2015, SPE, SPE-Duplex UMI, CAPP-Seq, iDES eCAPP-Seq, SLHC-Seq. Recently, several novel approaches have emerged. These include TARDIS, which is a hybrid of ligation and linear PCR, and ATOM-Seq, where UMI is added onto target via attaching and extending a loop-stem UMI adapter.

PCR-based technologies often use 2 to 3 cycles of PCR to assign one or a few UMIs to one target molecule, so that a quantitative ratio between UMI and the target is preserved. A limited number of PCR cycles is critical to avoid introducing redundant UMIs onto the same target molecule. However, this requirement hinders the amplification of the rare ctDNA targets to a level that is high enough for efficient downstream DNA manipulations. Ligation-based methods usually utilize unique approaches to minimize the loss of the precious ctDNA, maximize the efficiency of adapter ligation and avoid the base errors during end-repairing the target molecules. The requirement of quantitative assignment of UMI to target molecules also places a limit on the PCR amplification of the targets, unless the sequences of UMIs on both sense and antisense strands are complementary (such as in Duplex-Seq, discussed below). The limitation of target amplification contributes, at least partially, to the difficulties in sampling rare ctDNA targets.

One of the most important functions of UMI is its power to reduce random errors that are frequently observed in NGS. UMI allows condensing the sequences in each UMI clone into a consensus sequence, where the random errors on individual sequences are reduced. The majority of the above-mentioned methods organize the target molecules with UMI to form a one-dimensional UMI array, and deduce consensus sequence once. We call this category of techniques single consensus methods. However, single consensus is ineffective to remove errors, especially those in low (<0.5%) variant allele frequencies. The inefficient power of single consensus techniques exacerbates the problem of detecting rare mutations.

Duplex-Seq is a promising alternative, but also suffers from a number of problems. In addition to the one-dimensional array of UMIs, Duplex-Seq recognizes the complementary UMIs on both sense and antisense strand of the same molecule and forms a matrix of two-dimensional UMIs providing a double consensus technique. The complementary nature of the UMIs on both strands of the same molecule allows the target DNA to be well amplified from a few nanograms to the level of micrograms. This allows the targets to be easily enriched downstream by hybridization capture, and has demonstrated superior power in removing random errors, and detecting rare mutations with ultra-high sensitivity and accuracy. However, a major problem has persisted since its introduction. Duplex-Seq requires a complementary pair of UMIs on the same molecule to be recovered, however, the sequences of UMIs change (in other words, the random errors can occur in the sequences of UMIs) during the process of making the library and sequencing. Only ~5-15% of the recovered UMIs are recognizable to be complementary in Duplex-Seq. This major drawback requires a very large amount of DNA to be used in making library, as well as a significant sequencing read depth, resulting in a considerably high cost of sequencing.

The strategy of double consensus has demonstrated its power in enhancing sensitivity and accuracy, as well as the popularity of the method itself. It has further sparked many other attempts that utilize various approaches to reach the effect of a two-dimensional UMI matrix. These methods include a few improvements of the Duplex-Seq (e.g., BotSeqS, PECC-Seq, NanoSeq), several rolling circle amplification (RCA) related methods and Pro-Seq, which colonizes copies of the same target on the same molecule; BiSeqS, which creates strand asymmetry via bisulfite conversion;

MAPs, which splits a sample into two pools; and PhasED, which detects multiple mutations on one target.

Unfortunately, all of these techniques suffer from problems and disadvantages that may skew the results and add additional time and cost. What is needed are methods and compositions that may address these limitations.

SUMMARY OF THE DISCLOSURE

Described herein are methods and compositions (including kits), for reducing base errors in sequencing double-stranded DNA targets and methods of amplifying a plurality of target-specific double-stranded DNA targets. These methods may be referred to generally as "TriSeq" sequencing methods or TriSeq technology, and may address the major technical problems of existing UMI technologies: sensitivity and accuracy in detecting low quantities of ctDNA, low UMI utilization rate in double consensus, and high sequencing cost. These methods and compositions described herein allow for three rounds of reduction of random base errors. These methods place UMIs on one-side (either 5' or 3' end) of the target molecules. These methods and compositions allow low quantities of starting template DNA to be amplified into primary UMI clones without creating redundant UMIs. After amplification, these methods subdivide the primary UMI clones into subclones through a primer extension reaction with a panel of forward and reverse primers. Two rounds of noise reduction are carried out though finding consensus sequence from the sequences within each subclone of UMI, and the sequences within each primary UMI clone. A third round of noise reduction is carried out by finding similar variant calls between the reads derived from the forward primers and the reverse primers. These techniques do not require a complementary pair of UMIs to be recovered, nor a matched number of subclones representing the sense and antisense strand to co-exist within the primary UMI clone. These techniques may reach a high sensitivity and accuracy through initial DNA amplification and double consensus, and may significantly improve the efficiency of UMIs usage while reducing sequencing cost.

In general, the methods and compositions (including systems and kits) described herein relate to the amplification of nucleotide sequences, or the making of DNA libraries. In particular, the methods, compositions and systems described herein relate to increasing the sensitivity and accuracy of amplifying multiple different DNA fragments and reducing random errors of nucleotide incorporation during amplification and/or sequencing. The methods and compositions described herein may include analyzing unique molecular identifier (UMI) or molecular barcode and target DNA by massive parallel sequencing or high throughput sequencing (next generation sequencing, NGS).

Described herein are methods (e.g., strategies, techniques, etc.) and compositions (e.g., systems, kits, etc.) for generating highly sensitive and accurate sequencing results of massive parallel sequencing (NGS). The methods and compositions described herein may be referred to as TriSeq. TriSeq may comprise two parts (FIG. 1). The first part includes amplifying a plurality of target DNA fragments in the presence of dUTP, making a target-enriched DNA library by using a plurality of both forwards primers and reverse primers, organizing the UMIs on DNA molecules to form primary clones and subdividing the primary clones into subclones. The second part includes sequencing the DNA library by NGS and nucleotide sequence analysis.

The first part of the technique may include amplifying each of the target DNA molecule into a primary clone defined by UMIs attached onto them, and subdividing the primary clone into subclones by using a plurality of UMI-containing target-specific primers (the panel). In the first part, for example, the UMIs may be placed on specific positions of an adapter and each forward and reverse primer of a target-specific primer panel. The primary clones are formed through ligation of the UMI-containing adapter onto target DNA molecules, followed by PCR amplification in the presence of dUTP. Each of the primary clone is subdivided into subclones through the annealing and extension of the panel to the amplified DNA molecules. The template DNA fragments are then broken by making nick and breaks enzymatically at the dU sites. Single-stranded DNA regions and fragments are also removed simultaneously. Through further PCR amplification, a targeted DNA library is made after finishing the above process. In each primary clone, the DNA molecules share the same UMI sequence on one side of the molecules, while on the opposite side, the UMIs form multiple subclones. Since the panel comprises both forward and reverse primers, a set of the primary clones and the subclones is actually built on the forward primers, and a second set on the reverse primers. In a different phrasing of the same concept, the UMIs are organized into a three-dimensional matrix.

The second part of the technique may include sequencing the DNA library by massive parallel sequencing (high throughput sequencing, NGS), sorting the target specific primers on the molecules into a group of forward reads and a group of reverse reads, sorting the UMIs on one side of the molecules into primary clones inside each group, and sorting the UMIs on the other side of the molecules into subclones within each primary clone. These processes may include correcting base errors in the sequence of UMI and examining the length of the molecule and the end sequence on the side of the primary UMI. It further includes deducing consensus sequence within each subclone, deducing consensus sequence within each primary clone (from the consensus sequences obtained from subclones), finding similar variant calls between the forward group and the reverse group, and removing random errors associated with the library preparation and sequencing processes.

In one example, TriSeq starts from end repair and phosphorylating the 5' ends of the DNA fragments (FIG. 2). A single-stranded DNA-RNA hybrid adapter is then ligated to the 5' ends of the DNA fragments on both sides. The DNA adapter comprises a UMI region and a first universal primer binding site for PCR amplification. The DNA fragments are amplified with a universal primer in PCR in the presence of dUTP. The amplified DNA is then purified and the dUTP are removed. A panel of both forward and reverse target-specific primers is then annealed onto a large quantity of the amplified DNA fragments, followed by primer extension in the absence of dUTP, wherein each of these target-specific primers comprises a target-specific region, a UMI region and a second universal primer region, wherein at least two and up to one hundred thousand target-specific primers are included. The amplified template DNA fragments contain dU bases along the length. The dU bases are cleaved by uracil DNA glycosylase and apurinic/apyrimidinic endonuclease, leaving nicks on double-stranded DNA and breaks on single-stranded DNA. The resulting single-stranded DNA and/or the existing single-stranded DNA are reduced or removed simultaneously by a 3' to 5' single-stranded DNA specific exonuclease. The extended target DNA molecules, which are dU bases-free, are intact and amplified in a second PCR with a pair of universal primers. The sample indexes and sequencing adapters are simultaneously added during the second PCR. The finished library is ready for massive parallel sequencing.

In one example, a sample-index-containing UMI adapter is ligated onto the DNA fragments, and a hybridization capture of target molecules is applied following the amplification and pooling of samples (FIG. 3). TriSeq starts from end repair and phosphorylating the 5' ends of the DNA fragments. A single-stranded DNA-RNA hybrid adapter is then ligated to the 5' ends of the DNA fragments on both sides. The DNA adapter comprises a universal primer region, a UMI region and a sample index region. The DNA fragments are amplified with a universal primer in PCR in the presence of dUTP. Multiple samples with different sample indexes are amplified, pooled and purified. The target molecules are enriched by hybridization capture with a pool of target-specific probes. A panel of target-specific primers is then annealed onto the amplified DNA fragments, followed by extension in the absence of dUTP, wherein each of these target-specific primers comprises a target-specific region, a UMI region and a second universal primer region, wherein at least two and up to one hundred thousand target-specific primers are included, and wherein the target-specific primers are both forward and reverse PCR primers. The amplified template DNA fragments contain dU bases along the length. The dU bases are cleaved by uracil DNA glycosylase and apurinic/apyrimidinic endonuclease, leaving nicks on double-stranded DNA and breaks on single-stranded DNA. The resulting single-stranded DNA and/or the existing single-stranded DNA are reduced or removed simultaneously by a 3' to 5' single-stranded DNA specific exonuclease. The extended target DNA molecules, which are dU bases-free, are intact and amplified in a second PCR with a pair of universal primers. The sequencing adapter is simultaneously added during the second PCR. The finished library is ready for massive parallel sequencing.

In one example, part of this method is used to amplify a plurality of DNA targets. It starts from end repair and phosphorylating the 5' ends of the DNA fragments. A single-stranded DNA-RNA hybrid adapter is then ligated to the 5' ends of the DNA fragments on both sides. The DNA adapter comprises a universal primer region and optionally a UMI region. The DNA fragments are amplified with a universal primer in PCR in the presence of dUTP. The amplified DNA fragments are purified. A panel of target-specific primers is then annealed onto the amplified DNA fragments, followed by extension in the absence of dUTP, wherein each of these target-specific primers comprises a target-specific region, a second universal primer region and optionally a UMI region, wherein at least two and up to one hundred thousand target-specific primers are included, and wherein the target-specific primers are forward, or reverse, or both forward and reverse PCR primers. The amplified template DNA fragments contain dU bases along the length. The dU bases are cleaved by uracil DNA glycosylase and apurinic/apyrimidinic endonuclease, leaving nicks on double-stranded DNA and breaks on single-stranded DNA. The resulting single-stranded DNA and/or the existing single-stranded DNA are reduced or removed simultaneously by a 3' to 5' single-stranded DNA specific exonuclease. The extended target DNA molecules, which are dU bases-free, are intact and amplified in a second PCR with a pair of universal primers.

Any method and strategy of adapter design and ligation reactions, in which the UMIs on the adapter form clones through PCR amplification, may be used in the methods and compositions described herein. For example, ligating a single-stranded UMI-containing DNA adapter to the 5' ends of the DNA molecules, or ligating double-stranded UMI-containing DNA adapters to both ends of the DNA molecules, may be equally well suited for the strategies, systems, methods and compositions described herein. For a second example, the above mentioned single-stranded UMI-containing DNA adapter may contain a stretch of RNA bases, and/or contain modifications at its 5' and/or 3' end. For an example, the number of the RNA bases could be 3, or 4, or 5, or 6, or 7, or 8, or 9, or 10, or 11, or 12. For an example, the 5' modification could be 5'-amino-modifier C6 (5' AmMC6), or 5' inverted dideoxy-thymidine (5'-invddT), or other modifications. For a further example, the above mentioned double-stranded UMI-containing DNA adapter may contain a double-stranded region comprising a double-stranded UMI with complementary nucleotide sequence, or a Y-shaped UMI region comprising non-complementary UMIs. The above examples do not intend to exhaust the possibilities of the methods and strategies of adapter design and ligation reactions. There may exist an unlimited number of methods for attaching a UMI-containing adapter to the target DNA molecules. But they all fall within the concept of forming primary UMI clones and subdividing each primary UMI clone into subclones, and finally forming a three-dimensional matrix of UMIs.

Many other examples of the concepts of TriSeq are possible. These may include, but not limited to, using various adapters, using various combinations of PCR and hybridization capture, switching a region of nucleotide sequence through utilizing dU-containing primer and enzymatic manipulations, etc. It is almost impossible to exhaust the number and the types of these variations in details and in depictions. All of these examples, through various designs and technical approaches, may include the concept of dividing the reads obtained from NGS sequencing into a group containing forward primers and a group containing reverse primers, and in each read group forming primary UMI clones (or UMI clusters) and multiple UMI subclones (or subclusters) in each primary UMI clone.

In the foregoing examples, one or more of the method steps is conducted in manual mode or in an automated mode or a combination thereof. In particular examples each of the method steps is carried out in automated mode. In some examples the foregoing methods further comprise at least one purification step. In particular examples a purification step is carried out only after the second PCR. In other particular examples a purification is carried out after the digestion step and an additional purification is carried out after the second PCR. In some examples the hybridization capture method uses a plurality of biotin-labeled target-specific probes for enriching a subset of chosen molecules with streptavidin-coupled magnetic beads. In some of the examples the primer-dimer byproducts are removed from the resulting library. In some of the examples the primer-dimer byproducts are reduced from the resulting library. In certain examples, primer-dimer byproducts are eliminated. In some examples, the foregoing methods comprise a digestion reagent selected from any one or a combination of T4 endonuclease VII, T7 endonuclease I, endonuclease I, endonuclease V, Nth endonuclease III, endonuclease VII, endonuclease VIII, uracil DNA glycosylase (UDG), apurinic endonuclease (e.g., apurinic/apyrimidinic (AP) endonuclease 1(APE1)), RecJf, formamidopyrimidine [fapy]-DNA glycosylase (fpg), nuclease S1, nuclease P1, mung bean nuclease, nuclease CEL I, T4 DNA polymerase, T7 DNA polymerase, phi29 DNA polymerase. In some examples the foregoing methods comprise digestion reagent selected from any one or a combination of uracil DNA glycosylase (UDG), apurinic endonuclease (e.g., APE1), endonuclease III, endonuclease VIII and formamidopyrimidine [fapy]-DNA glycosylase (fpg). In some examples, the foregoing methods further comprise analyzing the nucleotide sequence of the resulting targeted DNA library. Such analysis comprises sequencing by traditional sequencing reactions (e.g., Danger sequencing), high throughput next generation sequencing, targeted multiplex array sequence detection, or any combination of two or more of the aforementioned methods. In some examples, the foregoing methods further comprise deducing the consensus sequence from each UMI cluster of at least one target molecule in the sample. In other examples, the foregoing methods further comprise determining the abundance of at least one of the target nucleic acid sequences in the sample. In specific examples, the foregoing methods further comprise determining the low frequency allele(s) in a sample.

The methods and compositions described herein may be used with and/or may modify those described in U.S. patent application Ser. No. 17/726,480, filed on Apr. 21, 2022, titled "METHODS AND COMPOSITIONS FOR AMPLIFYING DNA AND GENERATING DNA SEQUENCING RESULTS FROM TARGET-ENRICHED DNA MOLECULES". This application is herein incorporated by reference in its entirety.

For example, described herein are methods of reducing base errors in sequencing double-stranded DNA targets, wherein each primary clone of DNA target is subdivided into subclones along the course of DNA amplifications, wherein base errors are reduced after NGS sequencing by dividing the reads into a group reads containing the forward primers and a group of reads containing the reverse primers, finding consensus sequence in each subclone, then in each primary clone, and then finding similar variant calls between the forward group and the reverse group. In some examples, the method includes: forming primary clones from double-stranded DNA molecules by: ligating an adapter to the ends of a plurality of double-stranded DNA molecules, wherein the adapter comprises a UMI and a first universal primer binding site for PCR amplification, and the UMI comprises at least eight degenerate or semi-degenerate base sequence, and amplifying the adapter-DNA complexes with the universal primer in the presence of dUTP, resulting in each strand of the DNA molecule producing a clone of itself; subdividing each primary clone into subclones comprising: annealing and extending a plurality of target-specific primers to the primary clones in the absence of dUTP, wherein each of the target-specific primers comprises a target-specific region, a UMI and a second universal primer binding site for PCR amplification, resulting in each primary clone being subdivided into multiple subclones defined by the UMIs on the target-specific primers on one side of the resulting molecules, while each primary clone is still identifiable by the UMI from the adapter on the other side of the resulting molecules, enzymatically breaking the template DNA at the dU sites and removing the single-stranded regions from 3' ends in the above DNA structures, and amplifying the resulting products using a pair of second universal primers; and removing base errors after sequencing, comprising: sorting sequences into a forward group and a reverse group by the orientations of the target-specific primers, sorting sequences into primary clones by UMIs on the adapters on one side of the molecules, sorting each primary clone into subclones by the UMIs on the target-specific primers on the other side of the molecules, and deducing consensus sequence from each subclone, deducing consensus sequence in each primary clone from the consensus sequences obtained from the subclones within each primary clone, and finding similar variant calls between the forward group and the reverse group.

A method of reducing base errors in sequencing double-stranded DNA targets, wherein each primary clone of a DNA target is subdivided into subclones along the course of DNA amplifications, wherein base errors are reduced by finding consensus sequences in each subclone, then in each primary clone, and then finding similar variant calls between the forward group and the reverse group, may include: forming primary UMI clones from double-stranded DNA molecules by: ligating an adapter to the ends of a plurality of double-stranded DNA molecules, wherein the adapter comprises a UMI, a first universal primer binding site for PCR amplification and a sample index, wherein the UMI comprises at least eight degenerate or semi-degenerate base sequence; pooling samples and target enrichment by hybridization capture, including pooling together the adapter-DNA complexes of multiple samples, amplifying the adapter-DNA complexes with the universal primer in the presence of dUTP, resulting in each strand producing a clone of itself, followed by hybridization and capturing with a plurality of target-specific probes, wherein each of the target-specific probe is tagged with biotin moiety for capturing with streptavidin-coupled magnetic beads; subdividing each primary UMI clone into UMI subclones by: annealing and extending a plurality of target-specific primers to the primary UMI clones in the absence of dUTP, wherein each of the target primer comprises a target-specific region, a UMI and a second universal primer binding site for PCR amplification, resulting in each primary clone being subdivided into multiple subclones defined by the UMIs on the target primers on one side of the resulting molecules, while each primary clone is still identifiable by the UMI from the adapter on the other side of the resulting molecules; enzymatically breaking the template DNA at dU sites and removing the single-stranded regions from 3' ends in the above DNA structures; and amplifying the resulting products using a pair of second universal primers; and removing base errors after sequencing by: sorting sequences into a forward group and a reverse group by the orientations of the target-specific primers, sorting sequences into primary UMI clones by UMI on one side of the molecules and the sequences of the plurality of the amplified targets, sorting each primary clone into subclones by the UMI on the other side of the molecules, and deducing consensus sequence from each subclone, then deducing consensus sequence in each primary clone from the consensus sequences obtained from the subclones within each primary clone, and finding similar variant calls between the forward group and the reverse group.

In any of the methods described herein, ligating the adapter may further comprise: blunting ends and phosphorylating the 5' ends of the DNA molecules, and/or ligating a ssDNA adapter to the 5' end of the DNA molecules, and/or ligating a ssDNA-RNA hybrid adapter to the 5' end of the DNA molecules, and/or ligating one strand of dsDNA adapter to 5' end of the DNA molecules, and/or tagging a ssDNA adapter by template switching.

In any of these methods described herein, the degenerate or semi-degenerate bases in UMI of the adapter may have between 8 and 20 random bases.

Amplifying the adapter-DNA complexes may comprise amplifying with one universal primer by PCR or linear amplification. The universal primers may have one or multiple Us replacing Ts. The degenerate or semi-degenerate bases in the UMI of the target-specific primer may have between 3 and 20 random bases. The preferred numbers of the random bases in the UMI of the target-specific primers are 3, 4 and 5.

The plurality of target-specific primers may be a panel of reverse primers, or a panel of forward primers, or a panel of both forward and reverse primers. The number of the plurality of target-specific primers may be between 2-100,000.

In any of these examples, enzymatically breaking the template DNA and removing the single-stranded regions may comprise cleaving the Us in the template DNA by uracil DNA glycosylase (UDG) and apurinic/apyrimidinic endonuclease, leaving nicks at dU sites on double-stranded DNA and breaks at dU sites on single-stranded DNA, and removing single-stranded DNA regions and single-stranded DNA by using 3' to 5' single-strand DNA specific exonuclease. Apurinic/apyrimidinic endonucleases may include, but not limited to, APE 1, endonuclease III, endonuclease V, endonuclease VIII, and fpg.

In any of these methods, amplifying the resulting products may include adding sample indexes. Any of these methods may include hybridization capture after ligating the adapter to the DNA fragments, or after amplifying the adapter-DNA complexes. In any of these methods deducing consensus sequence may further comprise calculating allele frequency based on the number of clones of a specific mutation.

A method of amplifying a plurality of target-specific double-stranded DNA targets may include: amplifying a plurality of DNA molecules in the sample by: ligating an adapter to the ends of a plurality of double-stranded DNA molecules, wherein the adapter comprises a first universal primer binding site for PCR amplification and an optional UMI, and amplifying the adapter-target complexes with the universal primer in the presence of dUTP; and amplifying a plurality of target-specific double-stranded DNA targets by: annealing and extending a plurality of target-specific primers to the DNA molecules in the absence of dUTP, wherein each of the target primer comprises a target-specific region and a second universal primer binding site for PCR amplification, wherein each of the target primers may further comprise an optional UMI, and enzymatically breaking the template DNA and removing the single-stranded regions from 3' ends in the above DNA structures, and amplifying the resulting products using a pair of second universal primers.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

Definitions

Figure 1:
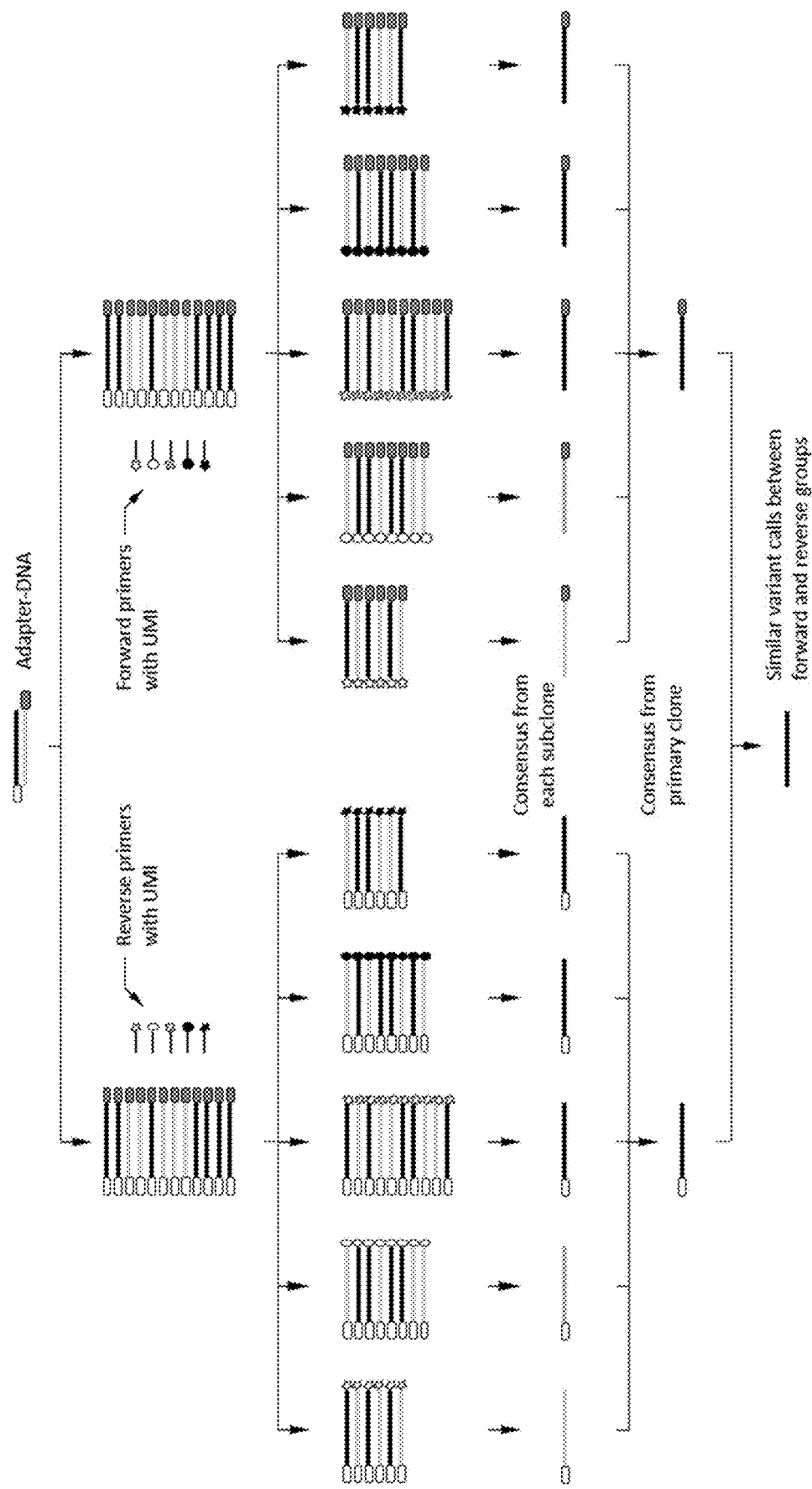
FIG. 1 schematically illustrates TriSeq, showing ligating a single-stranded DNA-RNA hybrid adapter to the 5' end of a double-stranded DNA fragment, amplifying the adapter-DNA complex, forming one primary UMI clone and multiple UMI subclones with DNA fragments containing forward target-specific primers, forming one primary UMI clone and multiple UMI subclones with DNA fragments containing reverse target-specific primers, and deducing one consensus sequence from each UMI subclone, deducing one consensus sequence within each primary UMI clone, and deducing the consensus sequence between the forward and reverse sequences.
Figure 2:
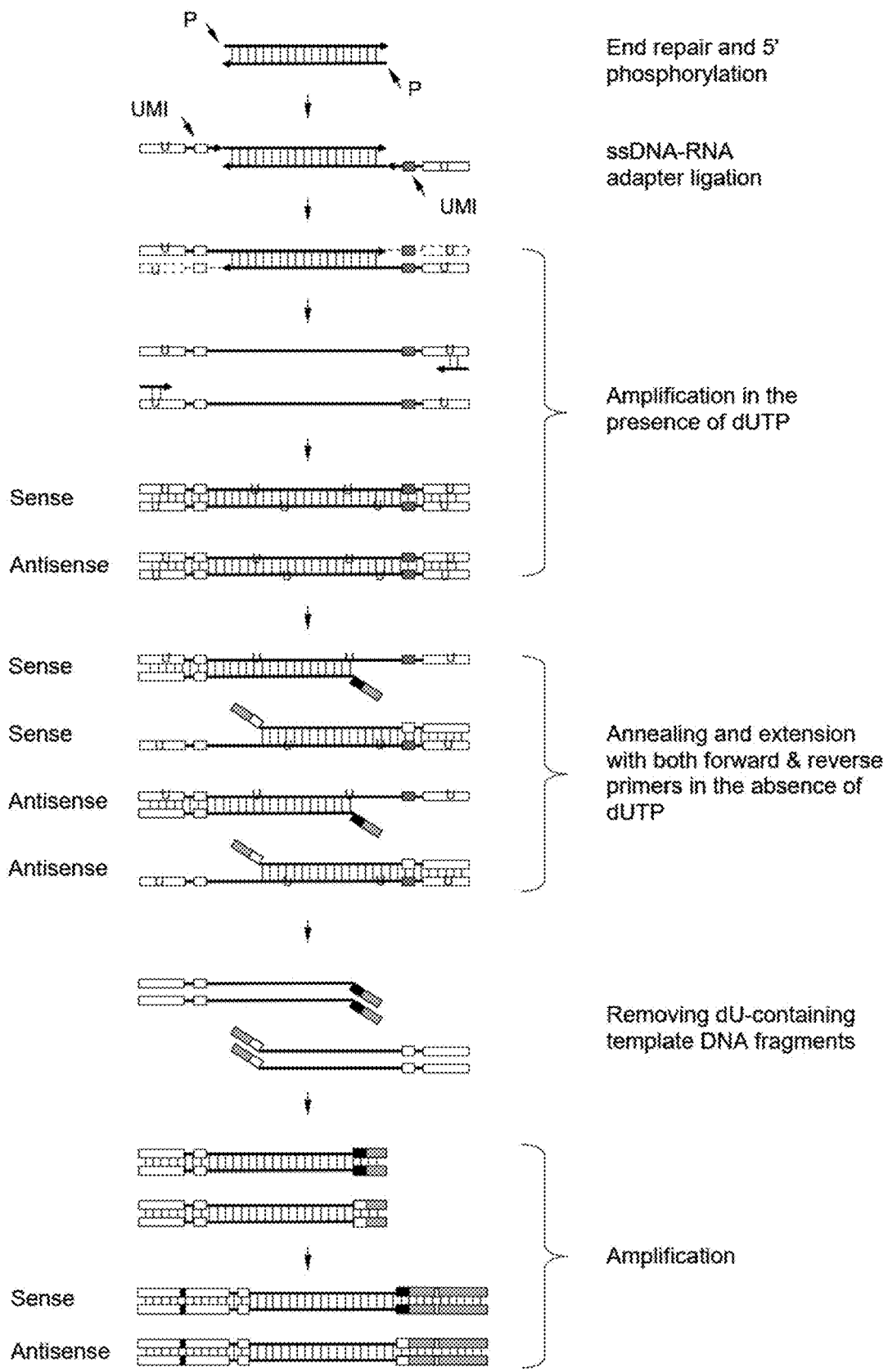
FIG. 2 schematically illustrates an example of TriSeq, ligating a single-stranded an adapter to the 5' end of double stranded DNA molecules, amplifying the ligated DNA fragments in the presence of dUTP, selecting the target molecules with a panel of target-specific primers and extending the targets in the absence of dUTP, removing dU-containing template DNA, and the final amplification of the target DNA library.
Figure 3:
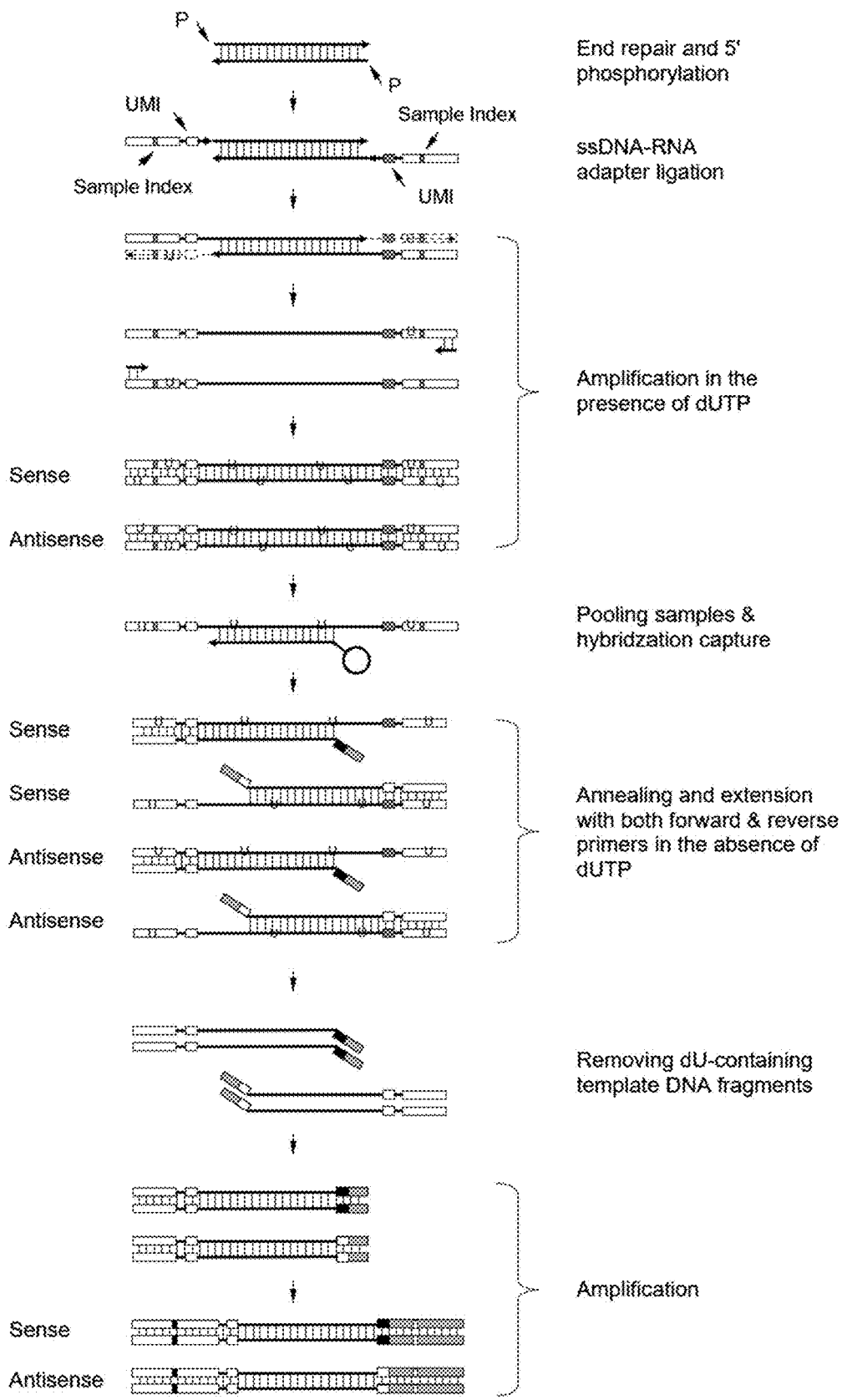
FIG. 3 schematically illustrates an example of TriSeq, employing hybridization capture to enrich the target molecules, where the target enrichment by hybridization capture is depicted after amplification of the adapter-DNA complex. Hybridization capture can also be done after the adapter ligation and before amplification of the adapter-DNA complex.

In general, described herein are strategies, systems, methods and compositions that may be used to generating highly sensitive and accurate sequencing results of NGS through the use of UMI. Unless otherwise defined, all technical and scientific terms used herein have the same meaning as commonly understood by one of ordinary skill in the art to which this invention belongs. Still, certain elements are defined for the sake of clarity and ease of reference.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization used herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. Techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). Unless specifically provided, any nomenclature utilized in connection with, and laboratory procedures and techniques described herein are those well-known and commonly used in the art. As utilized in accordance with embodiments provided herein, the following terms, unless otherwise indicated, shall be understood to have the following meanings:

As used herein, "amplify", "amplifying" or "amplification reaction" and their derivatives, refer generally to an action or process whereby at least a portion of a nucleic acid molecule (referred to as a template nucleic acid molecule) is replicated or copied into at least one additional nucleic acid molecule. The additional nucleic acid molecule optionally includes a sequence that is substantially identical or substantially complementary to at least some portion of the template nucleic acid molecule. A template target nucleic acid molecule may be single-stranded or double-stranded. The additional resulting replicated nucleic acid molecule may independently be single-stranded or double-stranded. In some examples, amplification includes a template-dependent in vitro enzyme-catalyzed reaction for the production of at least one copy of at least some portion of a target nucleic acid molecule or the production of at least one copy of a target nucleic acid sequence that is complementary to at least some portion of a target nucleic acid molecule. Amplification optionally includes linear or exponential replication of a nucleic acid molecule. In some examples, such amplification is performed using isothermal conditions; in other examples, such amplification can include thermocycling. In some examples, the amplification is a multiplex amplification that includes simultaneous amplification of a plurality of target sequences in a single amplification reaction. At least some target sequences can be situated on the same nucleic acid molecule or on different target nucleic acid molecules included in a single amplification reaction. In some examples, "amplification" includes amplification of at least some portion of DNA- and/or RNA-based nucleic acids, whether alone, or in combination. An amplification reaction can include single or double-stranded nucleic acid substrates and can further include any amplification processes known to one of ordinary skill in the art. In some examples, an amplification reaction includes polymerase chain reaction (PCR). In some examples, an amplification reaction includes isothermal amplification.

As used herein, "amplification conditions" and derivatives (e.g., conditions for amplification, etc.) generally refers to conditions suitable for amplifying one or more nucleic acid sequences.

Amplification can be linear or exponential. In some examples, amplification conditions include isothermal conditions or alternatively include thermocyling conditions, or a combination of isothermal and thermocycling conditions. In some examples, conditions suitable for amplifying one or more target nucleic acid sequences includes polymerase chain reaction (PCR) conditions. Typically, amplification conditions refer to a reaction mixture that is sufficient to amplify nucleic acids such as one or more target sequences, or to amplify an amplified target sequence ligated or attached to one or more adapters, e.g., an adapter-attached amplified target sequence. Generally, amplification conditions include a catalyst for amplification or for nucleic acid synthesis, for example a polymerase; a primer that possesses some degree of complementarity to the nucleic acid to be amplified; and nucleotides, such as deoxyribonucleoside triphosphates (dNTPs) to promote extension of a primer once hybridized to a nucleic acid. Amplification conditions can require hybridization or annealing of a primer to a nucleic acid, extension of the primer and a denaturing step in which the extended primer is separated from the nucleic acid sequence undergoing amplification. Typically, though not necessarily, amplification conditions can include thermocycling. In some examples, amplification conditions include a plurality of cycles wherein steps of annealing, extending and separating are repeated. Typically, amplification conditions include cations such as Mg++ or Mn++(e.g., $MgCl_2$, etc.) and can also optionally include various modifiers of ionic strength.

As used herein, "target sequence" "target nucleic acid sequence" or "target sequence of interest" and derivatives, refers generally to any single or double-stranded nucleic acid sequence that can be amplified or synthesized according to the disclosure, including any nucleic acid sequence suspected or expected to be present in a sample. In some examples, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some examples, the term refers to a nucleic acid sequence whose sequence identity, ordering or location of nucleotides is determined by one or more of the methods of the disclosure.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

As used herein, "contacting" and its derivatives, when used in reference to two or more components, refers generally to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses examples where A is first contacted with B then C, as well as examples where C is contacted with A then B, as well as examples where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. For example, "contacting A with B and C" can include examples wherein C is first contacted with A to form a first mixture, which first mixture is then contacted with B to form a second mixture, following which C is removed from the second mixture; optionally A can then also be removed, leaving only B. Where one or more of the referenced components to be contacted includes a plurality (e.g., "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target-specific primers can be contacted with a target sequence, then a polymerase, and then with other members of the plurality of target-specific primers) in any order or combination.

As used herein, the term "primer" and its derivatives refer generally to any polynucleotide that can hybridize to a target sequence of interest. In some examples, the primer can also serve to prime nucleic acid synthesis. Typically, a primer functions as a substrate onto which nucleotides can be polymerized by a polymerase; in some examples, however, a primer can become incorporated into a synthesized nucleic acid strand and provide a site to which another primer can hybridize to prime synthesis of a new strand that is complementary to the synthesized nucleic acid molecule. A primer may be comprised of any combination of nucleotides or analogs thereof, which may be optionally linked to form a linear polymer of any suitable length. In some examples, a primer is a single-stranded oligonucleotide or polynucleotide. (For purposes of this disclosure, the terms 'polynucleotide" and "oligonucleotide" are used interchangeably herein and do not necessarily indicate any difference in length between the two). In some examples, a primer is double-stranded. If double stranded, a primer is first treated to separate its strands before being used to prepare extension products. Preferably, the primer is a deoxyribonucleotide oligo. A primer must be sufficiently long to prime the synthesis of extension products. Lengths of the primers will depend on many factors, including temperature, source of primer and the use of the method. In some examples, a primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some examples, the primer is a deoxyribonucleotide oligo or an oligoribonucleotide. In some examples, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some examples, a primer can be paired with a compatible primer within an amplification or synthesis reaction to form a primer pair consisting or a forward primer and a reverse primer. In some examples, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some examples, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some examples, one end of an amplification or synthesis product is defined by the forward primer and the other end of the amplification or synthesis product is defined by the reverse primer. In some examples, where the amplification or synthesis of lengthy primer extension products is required, such as amplifying an exon, coding region, or gene, several primer pairs can be created than span the desired length to enable sufficient amplification of the region. In some examples, a primer can include one or more cleavable groups. In some examples, primer lengths are in the range of about 10 to about 60 nucleotides, about 12 to about 50 nucleotides and about 15 to about 40 nucleotides in length.

Typically, a primer is capable of hybridizing to a corresponding target sequence and undergoing primer extension when exposed to amplification conditions in the presence of dNTPs and a polymerase. In some instances, the particular nucleotide sequence or a portion of the primer is known at the outset of the amplification reaction or can be determined by one or more of the methods disclosed herein. In some examples, the primer includes one or more cleavable groups at one or more locations within the primer.

As used herein, "target-specific primer" and its derivatives, refers generally to a single-stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some examples, the target-specific primer is capable of hybridizing to at least a portion of its corresponding target sequence (or to a complement of the target sequence); such hybridization can optionally be performed under standard hybridization conditions or under stringent hybridization conditions. In some examples, the target-specific primer is not capable of hybridizing to the target sequence, or to its complement, but is capable of hybridizing to a portion of a nucleic acid strand including the target sequence, or to its complement. In some examples, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other examples, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some examples, the target-specific primer is substantially non-complementary to other target sequences present in the sample; optionally, the target-specific primer is substantially non-complementary to other nucleic acid molecules present in the sample. In some examples, nucleic acid molecules present in the sample that do not include or correspond to a target sequence (or to a complement of the target sequence) are referred to as "non-specific" sequences or "non-specific nucleic acids". In some examples, the target-specific primer is designed to include a nucleotide sequence that is substantially complementary to at least a portion of its corresponding target sequence. In some examples, a target-specific primer is at least 95% complementary, or at least 99% complementary, or identical, across its entire length to at least a portion of a nucleic acid molecule that includes its corresponding target sequence. In some examples, a target-specific primer can be at least 90%, at least 95% complementary, at least 98% complementary or at least 99% complementary, or identical, across its entire length to at least a portion of its corresponding target sequence. In some examples, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some examples, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some examples, the target-specific primer can be substantially non-complementary at its 3' end or its 5' end to any other target-specific primer present in an amplification reaction. In some examples, the target-specific primer can include minimal cross hybridization to other target-specific primers in the amplification reaction. In some examples, target-specific primers include minimal cross-hybridization to non-specific sequences in the amplification reaction mixture. In some examples, the target-specific primers include minimal self-complementarity. In some examples, the target-specific primers can include one or more cleavable groups located at the 3' end. In some examples, the target-specific primers can include one or more cleavable groups located near or about a central nucleotide of the target-specific primer. In some examples, one of more targets-specific primers includes only non-cleavable nucleotides at the 5' end of the target-specific primer. In some examples, a target-specific primer includes minimal nucleotide sequence overlap at the 3' end or the 5' end of the primer as compared to one or more different target-specific primers, optionally in the same amplification reaction. In some examples 1, 2, 3, 4, 5, 6, 7, 8, 9, 10 or more, target-specific primers in a single reaction mixture include one or more of the above examples. In some examples, substantially all of the plurality of target-specific primers in a single reaction mixture includes one or more of the above examples.

As used herein, the term "adapter" denotes a nucleic acid molecule that can be used for manipulation of a polynucleotide of interest. In some examples, adapters are used for amplification of one or more target nucleic acids. In some examples, the adapters are used in reactions for sequencing. In some examples, an adapter has one or more ends that lack a 5' phosphate residue. In some examples, an adapter comprises, consists of, or consist essentially of at least one priming site. Such priming site containing adapters can be referred to as "primer" adapters. In some examples, the adapter priming site can be useful in PCR processes. In some examples an adapter includes a nucleic acid sequence that is substantially complementary to the 3' end or the 5' end of at least one target sequences within the sample, referred to herein as a gene specific target sequence, a target-specific sequence, or target-specific primer. In some examples, the adapter includes nucleic acid sequence that is substantially non-complementary to the 3' end or the 5' end of any target sequence present in the sample. In some examples, the adapter includes single-stranded or double-stranded linear oligonucleotide that is not substantially complementary to a target nucleic acid sequence. In some examples, the adapter includes nucleic acid sequence that is substantially non-complementary to at least one, and preferably some or all of the nucleic acid molecules of the sample. In some examples, suitable adapter lengths are in the range of about 10-75 nucleotides, about 12-50 nucleotides and about 15-40 nucleotides in length. Generally, an adapter can include any combination of nucleotides and/or nucleic acids. In some aspects, adapters include one or more cleavable groups at one or more locations. In some examples, the adapter includes sequence that is substantially identical, or substantially complementary, to at least a portion of a primer, for example a universal primer. In some examples, adapters include a tag sequence to assist with cataloguing, identification or sequencing. In some examples, an adapter acts as a substrate for amplification of a target sequence, particularly in the presence of a polymerase and dNTPs under suitable temperature and pH.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some examples, the second polypeptide can include a reporter enzyme or a processivity-enhancing domain. Optionally, the polymerase can possess 5' exonuclease activity or terminal transferase activity. In some examples, the polymerase can be optionally reactivated, for example through the use of heat, chemicals or re-addition of new amounts of polymerase into a reaction mixture. In some examples, the polymerase can include a hot-start polymerase and/or an aptamer-based polymerase that optionally can be reactivated.

The terms' "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some examples, at least 50%, but less than 100%, of the residues of one nucleic acid sequence are complementary to residues in the other nucleic acid sequence. In some examples, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some examples, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some examples, two non-complementary or substantially non-complementary sequences cannot hybridize to each other under standard or stringent hybridization conditions. A "mismatch" is present at any position in the two opposed nucleotides are not complementary. Complementary nucleotides include nucleotides that are efficiently incorporated by DNA polymerases opposite each other during DNA replication under physiological conditions. In a typical example, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers generally to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure, amplified target sequences are typically less than 50% complementary to any portion of another amplified target sequence in the reaction.

As used herein, terms "ligating", "ligation" and derivatives refer generally to the act or process for covalently linking two or more molecules together, for example, covalently linking two or more nucleic acid molecules to each other. In some examples, ligation includes joining nicks between adjacent nucleotides of nucleic acids. In some examples, ligation includes forming a covalent bond between an end of a first and an end of a second nucleic acid molecule. In some examples, for example examples wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some examples, any means for joining nicks or bonding a 5' phosphate to a 3' hydroxyl between adjacent nucleotides can be employed. In an exemplary example, an enzyme such as a ligase can be used.

As used herein, "ligase" and its derivatives, refers generally to any agent capable of catalyzing the ligation of two substrate molecules. In some examples, the ligase includes an enzyme capable of catalyzing the joining of nicks between adjacent nucleotides of a nucleic acid. In some examples, a ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase 1; CircLigase II; T4 DNA ligase; T7 DNA ligase; Taq DNA ligase, and *E. coli* DNA ligase.

As defined herein, a "cleavable group" generally refers to any moiety that once incorporated into a nucleic acid can be cleaved under appropriate conditions. For example, a cleavable group can be incorporated into a target-specific primer, an amplified sequence, an adapter or a nucleic acid molecule of the sample. In an exemplary example, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adapter or a nucleic acid molecule of the sample by any acceptable means. For example, a cleavable group can be removed from a target-specific primer, an amplified sequence, an adapter or a nucleic acid molecule of the sample by enzymatic, thermal, photo-oxidative or chemical treatment. In one aspect, a cleavable group can include a nucleobase that is not naturally occurring. For example, a deoxyribonucleotide oligo can include one or more RNA nucleobases, such as uracil that can be removed by an uracil glycosylase. In some examples, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one example, a cleavable group can include a moiety that can be removed from a primer after amplification (or synthesis) upon exposure to ultraviolet light (i.e., bromodeoxyuridine). In another example, a cleavable group can include methylated cytosine. Typically, methylated cytosine can be cleaved from a primer for example, after induction of amplification (or synthesis), upon sodium bisulfite treatment. In some examples, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adapter or a nucleic acid molecule of the sample.

As used herein, "digestion", "digestion step" and its derivatives, generally refers to any process by which a cleavable group is cleaved or otherwise removed from a target-specific primer, an amplified sequence, an adapter or a nucleic acid molecule of the sample. In some examples, the digestion step involves a chemical, thermal, photo-oxidative or digestive process.

As used herein, the term "hybridization" is consistent with its use in the art, and generally refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some examples, at least one of the nucleic acid molecules can include portions that are not hybridized to the other nucleic acid molecule. The phrase "hybridizing under stringent conditions" and its variants refers generally to conditions under which hybridization of a target-specific primer to a target sequence occurs in the presence of high hybridization temperature and low ionic strength. As used herein, the phrase "standard hybridization conditions" and its variants refers generally to conditions under which hybridization of a primer to an oligonucleotide (i.e., a target sequence), occurs in the presence of low hybridization temperature and high ionic strength. In one exemplary example, standard hybridization conditions include an aqueous environment containing about 100 mM magnesium sulfate, about 500 mM Tris-sulfate at pH 8.9, and about 200 mM ammonium sulfate at about 50-55° C., or equivalents thereof.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some examples, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some examples, the 3' end does not include any unlinked 3' hydroxyl group but can include any moiety capable of serving as a site for attachment of nucleotides via primer extension and/or nucleotide polymerization. In some examples, the term "3' end" for example when referring to a target-specific primer, can include the terminal 10 nucleotides, the terminal 5 nucleotides, the terminal 4, 3, 2 or fewer nucleotides at the 3' end. In some examples, the term "3' end" when referring to a target-specific primer can include nucleotides located at nucleotide positions 10 or fewer from the 3' terminus. As used herein, "5' end", and its derivatives, generally refers to an end of a nucleic acid molecule, for example a target sequence or amplified target sequence, which includes a free 5' phosphate group or its equivalent. In some examples, the 5' end includes a 5' phosphate group that is not linked to a 3' hydroxyl of a neighboring mononucleotide pentose ring.

Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary example, the 5' end can include about 15 nucleotides adjacent to the nucleotide including the terminal 5' phosphate. In some examples, the 5' end does not include any unlinked 5' phosphate group but can include any moiety capable of serving as a site of attachment to a 3' hydroxyl group, or to the 3' end of another nucleic acid molecule. In some examples, the term "5' end" for example when referring to a target-specific primer, can include the terminal 10 nucleotides, the terminal 5 nucleotides, the terminal 4, 3, 2 or fewer nucleotides at the 5'-end. In some examples, the term "5' end" when referring to a target-specific primer can include nucleotides located at positions 10 or fewer from the 5' terminus. In some examples, the 5' end of a target-specific primer can include only non-cleavable nucleotides, for example nucleotides that do not contain one or more cleavable groups as disclosed herein, or a cleavable nucleotide as would be readily determined by one of ordinary skill in the art. A "first end" and a "second end" of a polynucleotide refer to the 5' end or the 3' end of the polynucleotide. Either the first end or second end of a polynucleotide can be the 5' end or the 3' end of the polynucleotide; the terms "first" and "second" are not meant to denote that the end is specifically the 5' end or the 3' end.

As used herein "UMI," "barcode," "index" or "tag sequence" and its derivatives, refers generally to a unique short (6-20 nucleotide) nucleic acid sequence within an adapter or primer that can act as a 'key' to distinguish or separate a plurality of amplified target sequences in a sample. For the purposes of this disclosure, a barcode or unique tag sequence is incorporated into the nucleotide sequence of an adapter or primer. As used herein, "barcode sequence" denotes a nucleic acid fixed sequence that is sufficient to allow for the identification of a sample or source of nucleic acid sequences of interest. A barcode sequence can be, but need not be, a small section of the original nucleic acid sequence on which the identification is to be based. In some examples a barcode is 6-20 nucleic acids long. In some examples, the barcode is comprised of analog nucleotides, such as L-DNA, LNA, PNA, etc. As used herein, "unique tag sequence" denotes a nucleic acid sequence having at least one random sequence and at least one fixed sequence. A unique tag sequence, alone or in conjunction with a second unique tag sequence, is sufficient to allow for the identification of a single target nucleic acid molecule in a sample. A unique tag sequence can, but need not, comprise a small section of the original target nucleic acid sequence. In some examples a unique tag sequence is 2-50 nucleotides or base pairs, or 2-25 nucleotides or base pairs, or 2-16 nucleotides or base-pairs in length. A unique tag sequence can comprise at least one random sequence interspersed with a fixed sequence.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g., 3'-5' and 2'-5', inverted linkages, e.g., 3'-3' and 5'-5', branched structures, or analog nucleic acids. Polynucleotides have associated counter ions, such as H+, NH4+, trialkylammonium, Mg2+, Na+ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g., 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever an oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "LP denotes deoxyuridine. As discussed herein and known in the art, oligonucleotides and polynucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured, and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of 32P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least two pairs of target-specific primers. In some examples, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some examples, the plexy can be about 5-plex, 10-plex, 50-plex, 100-plex, 500-plex, 1,000-plex, 5,000-plex, 10,000-plex, 15,000-plex, 20,000-plex or higher.

Methods for Making Libraries with or without UMI

The methods and compositions described herein may include information about the mechanism and technical details for the preparation of multiplexed, UMI-containing libraries suitable for massive parallel sequencing and downstream analysis. The methods described herein may also be utilized for the purpose of amplifying a plurality of DNA targets without UMI. The methods additionally allow for incorporation of dUTP, hybridization capture, etc., if so desired. Certain methods comprise streamlined and use-friendly workflows.

In one example, methods for preparing a UMI-containing library of target nucleic acid sequences are provided. In some examples, methods comprise removing the 3' protruding ends and phosphorylating the 5' ends of the DNA fragments; ligating a single-stranded DNA-RNA hybrid adapter to the 5' ends of the DNA fragments on both sides; amplifying the DNA fragments with a universal primer in PCR in the presence of dUTP; annealing and extending a panel of target-specific forward and reverse primers onto the amplified DNA fragments in the absence of dUTP; enzymatically breaking the template DNA and removing the single-stranded regions as well as the remaining primers and primer-dimers; further amplifying the target DNA molecules with a second PCR with a pair of universal primers. The DNA adapter used in the methods herein comprises a UMI region and a universal primer binding site. Each of the target-specific primers of the panel comprises a target-specific region, a UMI region and a second universal primer binding site, wherein at least two and up to one hundred thousand target-specific pair of primers are included, and wherein the target-specific primers are both forward and reverse PCR primers. The pair of universal primers comprises sample indexes and sequencing primers that are simultaneously added onto the DNA targets during the second PCR. The finished library is ready for massive parallel sequencing.

In some examples, the DNA adapter used in the methods herein comprises a universal primer region, a sample index, and a UMI region. Multiple samples with different sample indexes are pooled after adapter ligation and amplification by the universal primer in the presence of dUTP. A hybridization capture of target molecules by a pool of target-specific probes is applied following the pooling of samples. The methods comprise removing the 3' protruding ends and phosphorylating the 5' ends of the DNA fragments; ligating a single-stranded DNA-RNA hybrid adapter to the 5' ends of the DNA fragments on both sides; amplifying the DNA fragments with a universal primer in the presence of dUTP by PCR, and pooling multiple samples with different sample indexes; enriching the target molecules by hybridization capture with a pool of target-specific probes; annealing and extending a panel of target-specific primers onto the amplified DNA fragments in the absence of dUTP; enzymatically breaking the template DNA and removing the single-stranded regions as well as the remaining primers and primer-dimers; further amplifying the target DNA molecules in a second PCR with a pair of universal primers. Each of the target-specific primers of the panel comprises a target-specific region, a UMI region and a second universal primer region, wherein at least two and up to one hundred thousand target-specific primers are included, and wherein the target-specific primers are both forward and reverse PCR primers. The pair of universal primers comprises sample indexes and sequencing primers that are simultaneously added onto the DNA targets during the second PCR. The finished library is ready for massive parallel sequencing.

In certain examples, the methods described herein may include procedures that are utilized for the purpose of amplifying a plurality of DNA targets. The methods comprise removing the 3' protruding ends and phosphorylating the 5' ends of the DNA fragments; ligating a single-stranded DNA-RNA hybrid adapter to the 5' ends of the DNA fragments on both sides; amplifying the DNA fragments with a universal primer in PCR in the presence of dUTP; annealing and extending a panel of target-specific primers onto the amplified DNA fragments in the absence of dUTP; enzymatically breaking the template DNA and removing the single-stranded regions as well as the remaining primers and primer-dimers; and optionally further amplifying the target DNA molecules in a second PCR with a pair of universal primers. The DNA adapter comprises a universal primer region, and optionally a UMI region. Each of the target-specific primers comprises a target-specific region, a second universal primer region and optionally a UMI region, wherein at least two and up to one hundred thousand target-specific primers are included, and wherein the target-specific primers are forward, or reverse, or both forward and reverse PCR primers.

In some examples, many methods and strategies of adapter design and ligation reactions are utilized in the methods described herein. These methods and strategies include, but not limited to, ligating a single-stranded UMI-containing DNA adapter to the 5' ends of the DNA molecules, ligating a double-stranded UMI-containing DNA adapter to the both ends of the DNA molecules. In some examples, the above mentioned single-stranded UMI-containing DNA adapter contains a stretch of RNA, comprising 3-12 RNA bases, at 3' end. For an example, the number of the RNA bases could be 3, or 4, or 5, or 6, or 7, or 8, or 9, or 10, or 11, or 12. In some examples, the above mentioned single-stranded UMI-containing DNA adapter contains modifications at 5' and/or 3' end. For an example, the 5' modification could be 5'-amino-modifier C6 (5' AmMC6), or 5' inverted dideoxy-thymidine (5'-invddT), or other modifications. In some examples, the above mentioned UMI-containing DNA adapter contains a double-stranded region comprising a double-stranded UMI with complementary nucleotide sequence, or a Y-shaped UMI region comprising non-complementary UMI. The above examples do not intend to exhaust the possibilities of the methods and strategies of adapter design and ligation reactions. The above examples do not intend to exhaust the possibilities of the methods and strategies of adapter design and ligation reactions. There may exist an unlimited number of methods for attaching a UMI-containing adapter to the target DNA molecules. But they all fall within the concept of forming primary UMI clones and subdividing each primary UMI clone into subclones, and finally forming a three-dimensional matrix of UMIs.

Many other examples of the concepts of TriSeq are possible. These may include, but not limited to, using a panel of forward target-specific primers, or a panel of reverse target-specific primers, or a panel of both forward and reverse target-specific primers, using various adapters, using various combinations of PCR and hybridization capture, switching a region of nucleotide sequence through utilizing dU-containing primer and enzymatic manipulations, etc. It is almost impossible to exhaust the number and the types of these variations in details and in depictions. All of these examples, through various designs and technical approaches, materialize the concept of dividing a primary UMI clone (or UMI cluster) derived from a double-stranded DNA molecule or a single-stranded DNA molecule into multiplex UMI subclones (or subclusters).

In some examples, the large (Klenow) fragment of DNA polymerase I is used to make blunt ends, and T4 Polynucleotide Kinase is used to phosphorylate the 5' ends of the DNA fragments in the end repair reactions. In some examples, 1× Ligation buffer (50 mM Tris-HCl, pH7.5, 10 mM $MgCl_2$, 0.5 mM ATP, 5 mM DTT) is used in the end repair reactions. Blunting ends and phosphorylation reactions may be done sequentially, or combined in a single reaction. Klenow fragment of DNA polymerase I may introduce base errors at the ends of DNA fragments. In some examples, Exonuclease VII is used to shorten the 5' and 3' overhang to ≤7 nucleotides, then T4 DNA polymerase is used to blunt both ends in the presence of dNTP. In some examples, exonuclease T (Also known as RNase T) is used to remove 3' protruding ends to avoid the base errors introduced by Klenow fragment. In this case, a single-stranded adapter is ligated to the resulting 5' blunt ends and the preexisting 5' protruding ends of the DNA fragments. In some examples, mung bean nuclease (NEB M0250L), the buffers and the conditions suggested by the supplier are used to make blunt ends. In some examples, the end repair reactions are incubated at 25° C. for 40 minutes and the enzymes are subsequently inactivated at 65° C. for 20 minutes. In some examples, the damaged bases are repair simultaneously by a cocktail of enzymes, which include but not limited to endonuclease IV, formamidopyrimidine [fapy]-DNA glycosylase, uracil-DNA glycosylase, T4 pyrimidine DNA glycosylase and endonuclease VIII.

In some examples, a single-stranded DNA adapter is ligated to the DNA fragments. In some examples, the single-stranded DNA adapter comprises a universal primer region, a UMI region, and a short stretch of RNA. In some cases, the UMI region comprises 16 random bases and the short stretch of RNA comprises four ribonucleotides, such as rArArArA. In some cases, the UMI region comprises 12 random bases and the short stretch of RNA comprises four random ribonucleotides, such as rNrNrNrN. T4 RNA Ligase 1 (NEB M0204L) is used to ligate the single-stranded DNA adapter to the 5' blunt ends and the preexisting 5' protruding ends of the DNA fragments. In some examples, the adapter and T4 RNA Ligase 1 are added to the end repair reactions. In some cases, the ligation reaction is supplemented with 10-20% PEG3000, or 10-20% PEG6000, or 10-20% PEG8000. In some cases, the ligation reaction is additionally supplemented with 10-20% DMSO. In some cases, the ligation reaction is incubated at 37° C. for 2 hours, or at 37°C for 4 hours, or at 25° ° C. for 2 hours, or at 25° C. for 4 hours, or at 16° C. for 8 hours, or at 16° C. for 16 hours, or at 16°C for 24 hours. In some cases, the enzymes in the ligation reaction are subsequently inactivated at 65° C. for 20 minutes.

In some examples, the remaining single-stranded DNA adapters in the ligation reaction are removed after the ligation reaction. In some cases, exonuclease T is used to digest the remaining single-stranded DNA adapters by incubating at 25° C. for 40 minutes and 65° C. for 20 minutes.

In some examples, the DNA fragments are amplified with a universal primer in the presence of dUTP in PCR after the ligation. In some cases, the universal primer contains one dU base, or two dU bases, or three dU bases, or four dU bases. These dU bases replace the preexisting deoxythymidines. In some cases, the universal primer does not contain dU base.

Selecting DNA Polymerase that can Use RNA as Template.

Figure 4:
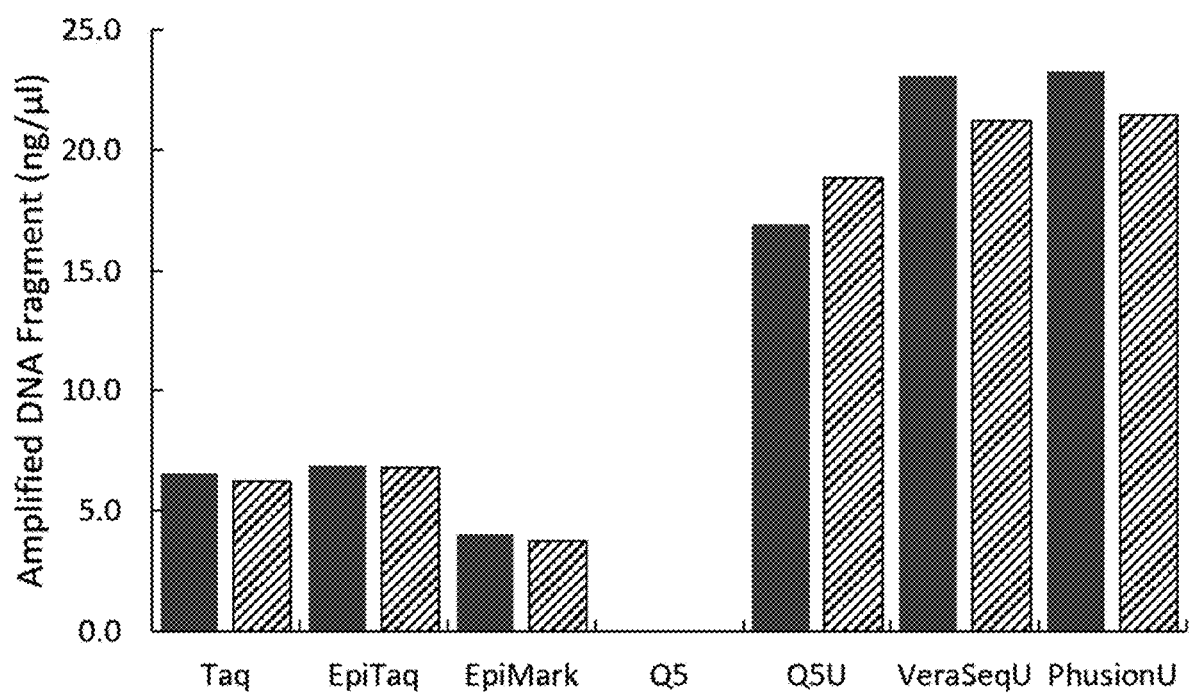
FIG. 4 shows that Taq and Taq-derived, dU-tolerant DNA polymerase use four RNA bases as template for DNA synthesis. Non-Taq-derived dU-tolerant DNA polymerases also use four RNA bases as template for DNA synthesis. The yields of the non-Taq-derived dU-tolerant DNA polymerases were over three-fold higher than the yields of Taq and Taq-derived DNA polymerases. A non-Taq-derived DNA polymerases, Q5 DNA polymerase, which is not dU-tolerant, does not amplify DNA in the presence of dNTP or dUTP.

The ligation of the single-stranded DNA-RNA hybrid adapter introduces four RNA bases on both side of the target DNA molecules. In order to amplify these RNA-containing DNA fragments, a DNA polymerase that uses both DNA and RNA as template must be used. Because dUTP is going to be incorporated into the DNA fragments during the amplification, this DNA polymerase should be capable of incorporating dUTP and using dU-containing DNA as template as well. It is known that Taq DNA polymerase and Taq-derived polymerases synthesize DNA over a short region of RNA template. They incorporate dUTP as well. A handful of engineered non-Taq-derived DNA polymerases, which are labeled as dU-tolerant, incorporate dUTP and use dU-containing DNA as template. To screen for DNA polymerases that meet the above requirements, we tested a group of dU-tolerant DNA polymerases in amplifying a 175 bp DNA fragment. Ligation of the DNA-RNA hybrid adapter onto one side or both sides results a 213 bp or 251 bp fragment, respectively. The universal primer amplifies the 251 bp fragment. The length of the resulting fragment from the amplification was confirmed by using a BioAnalyzer chip. We found that Taq, as well as the Taq-derived EpiTaq and EpiMark, amplified the DNA fragment in the presence of dNTP, indicating that these polymerases can use four RNA bases as template (FIG. 4). These polymerases also amplified the 251 bp in the presence of dUTP (FIG. 4, hatched bars). As expected, a non-Taq DNA polymerase, Q5 DNA polymerase, could not amplify the 251 bp DNA fragment in the presence of both dNTP and dUTP. All non-Taq-derived dU-tolerant DNA polymerases amplified the 251 bp DNA fragment either in the presence of dNTP or dUTP (FIG. 4). The yields of the non-Taq-derived dU-tolerant DNA polymerases were over three-fold higher than the yields of Taq and Taq-derived DNA polymerases. These non-Taq-derived dU-tolerant DNA polymerases are Q5U® Hot Start High-Fidelity DNA Polymerase, Phusion™ U Hot Start DNA Polymerase and VeraSeq Ultra DNA Polymerase.

Figure 5:
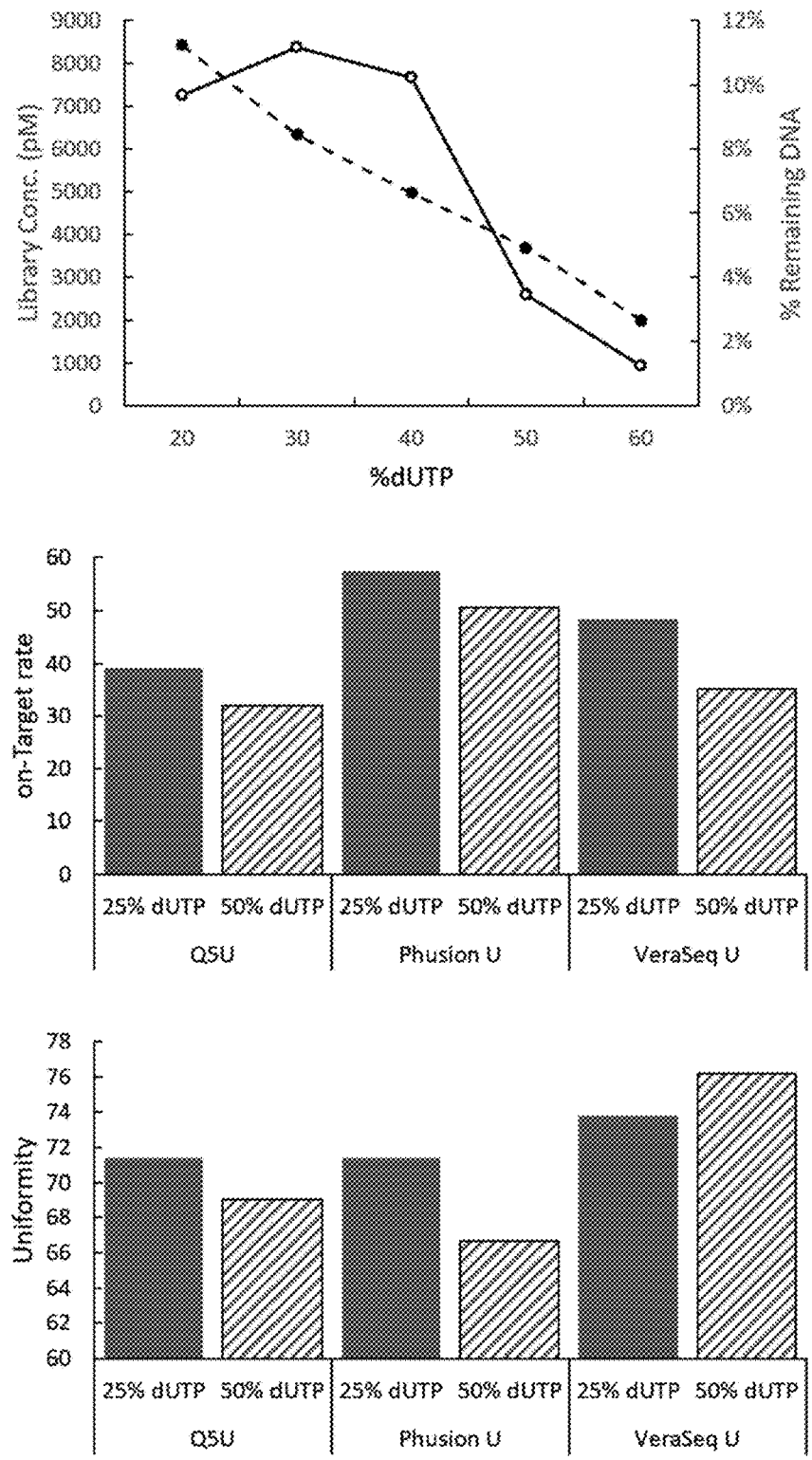
FIG. 5 shows that when DNA fragments are amplified with 60% dUTP, a higher percentage of the dU-containing template DNA is removed than the DNA amplified with 20% dUTP. However, the highest yield of DNA library is obtained with the DNA amplified with 30% dUTP. The sequencing qualities are better with the DNA fragments are amplified with 25-30% dUTP than with higher percentages of dUTP.

Amplify the Ligated DNA in the Presence of dUTP.

dUTP is incorporated into DNA during the amplification of the template DNA molecules. The dU-containing template DNA was subsequently destroyed enzymatically after the target DNA molecules are converted into non-dU-containing DNA molecules. In order to find the optimal concentration of dUTP, we titrated the percentage of dUTP in the range of 20-100% in the amplification reaction. The effect of percentage of dUTP on the digestion of dU-containing DNA molecules was evaluated by measuring the resulting DNA after digestion. The final libraries were sequenced, and the effect of percentage of dUTP on the quality of the final library was additionally evaluated by calculating the on-target rates and the uniformity. We found that 60% dUTP in the amplification reaction helped removing 97% of template DNA. In this circumstance, only 3% of the input DNA remained after the digestion. At 20% of dUTP, about 8% DNA remained after the digestion. However, the highest yield of library was found at 30% dUTP (FIG. 5). The highest on-target rate was found at 30% dUTP as well. To further confirm the above findings, we compared the effect of 25% and 50% dUTP on the on-target rate and uniformity by using three dU-tolerant DNA polymerases. Higher on-target rate was again found with all three dU-tolerant DNA polymerases, and higher uniformity was found with two dU-tolerant DNA polymerases (FIG. 5).

Figure 6:
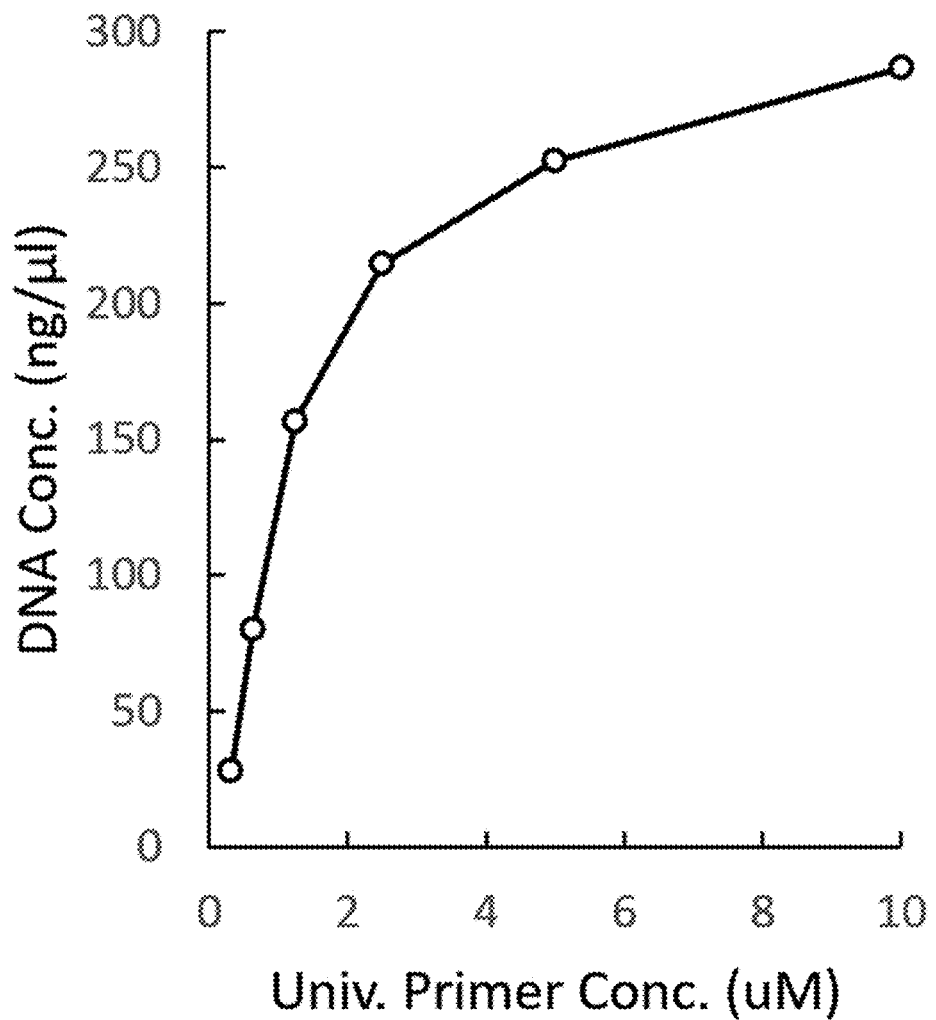
FIG. 6 shows the titration of the concentration of the universal primer that is used to amplify the DNA fragments. The optimal concentration of the universal primer is 10 μM, where the yield of DNA fragment is the highest, and the length of the DNA fragment is correct.

To find the optimal concentration of the universal primer that was used to amplify the RNA-containing DNA fragment, the 175 bp DNA fragment, as well as a mixture of sheared DNA fragments with peak length of 200 bp, was amplified with the universal primer at 0.3-10 μM. The yields were measured by a NanoDrop and the sizes were confirmed in a BioAnalyzer chip. The optimal concentration of the universal primer was found to be 10 μM (FIG. 6). At 10 μM of the universal primer, the yield of DNA fragment was the highest, and the length of the DNA fragment was correct.

Figure 7:
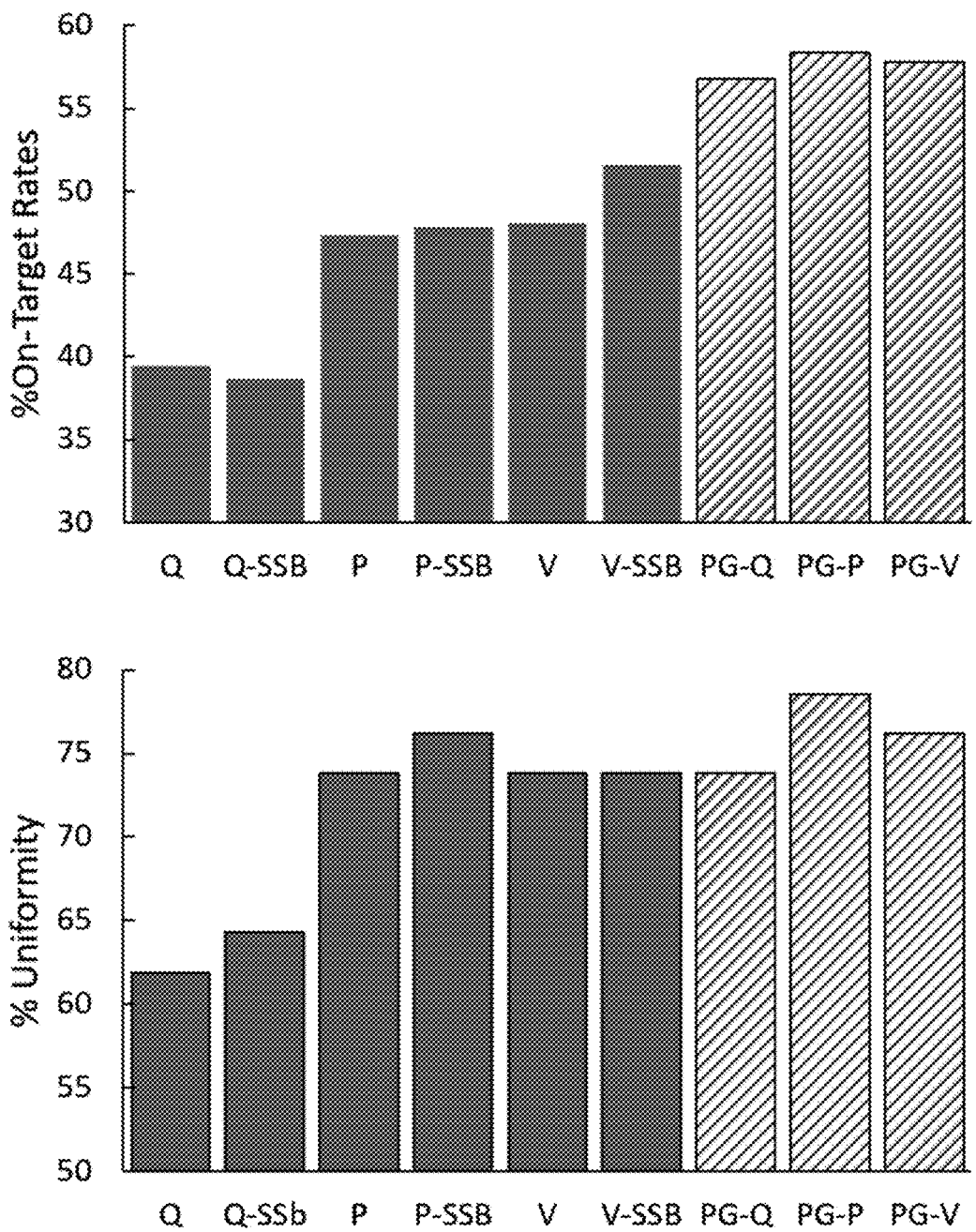
FIG. 7 shows the selection of the buffers that are used to amplify the DNA fragments. The sequencing qualities of the resulting libraries are generally better when the DNA polymerases are used in PG Buffer than in other kinds of buffers.

To amplify the RNA-containing DNA fragments in the presence of dUTP, we additionally screened the buffers for the dU-tolerant DNA polymerases with the goals of generating the highest on-target rate and uniformity. We chose non-Taq-derived dU-tolerant DNA polymerases based on their higher yields against Taq and Taq-derived dU-tolerant DNA polymerases. For all three dU-tolerant DNA polymerases, we found that the PG buffer produced higher on-target rates than the supplier's buffers for the dU-tolerant DNA polymerases (FIG. 7). PG buffer and the supplier's buffer generated comparable uniformity values for Phusion U and VeraSeq Ultra DNA polymerases. Single-stranded DNA binding protein (SSB) was reported to improve the performance of VeraSeq Ultra DNA polymerase. SSB helped on-target rate of VeraSeq Ultra DNA polymerase, but the value was still lower than those obtained with PG buffer. SSB may also help uniformity of Q5U and Phusion U DNA polymerases. However, those values were still lower than the uniformities of these polymerases in PG buffer.

Primer Extension with the Panel in the Absence of dUTP.

A primer extension reaction is used to capture the targeted DNA fragments from the dU-containing DNA fragments. The primer extension reaction is carried out in the absence of dUTP, so that the vast majority of the template DNA could be removed through digestion at dU positions, and the target DNA fragments in interest survive. The dU-tolerant DNA polymerases were used to us the dU-containing DNA as template, together with a plurality of both forward and reverse target-specific primers. The primer extension reaction is equivalent to a multiplex PCR that is executed in one cycle. Therefore, the reaction is required to be uniformity and specific. We used CleanPlex multiplex PCR buffer for the primer extension reaction.

Removing dU-Containing Template DNA and Amplification of the Resulting DNA Library After capturing the targeted DNA fragments in the primer extension reaction, the non-target DNA fragments are rendered un-amplifiable through making breaks at the sites of dUs. This is done by incubating a combination of UDG (uracil-DNA glycosylase), fpg (formamidopyrimidine [fapy]-DNA glycosylase) and Exonuclease I with the dU-containing DNA at 37° ° C. for 20~40 minutes. The remaining targeted DNA fragments (the library) is further amplified in a PCR reaction. The sample indexes are assigned into each sample during this PCR amplification.

In some embodiments the foregoing methods comprise digestion reagent selected from any one or a combination of T4 endonuclease VII, T7 endonuclease I, endonuclease I, endonuclease V, Nth endonuclease III, endonuclease VII, endonuclease VIII, UDG, apurinic endonuclease (e.g., APE1), RecJf, fpg, nuclease S1, nuclease P1, mung bean nuclease, nuclease CEL I, T4 DNA polymerase, T7 DNA polymerase, phi29 DNA polymerase. In some embodiments the foregoing methods comprise digestion reagent selected from any one or a combination of UDG, apurinic endonuclease (e.g., APE1) and fpg.

Sequencing Results.

Figure 8:
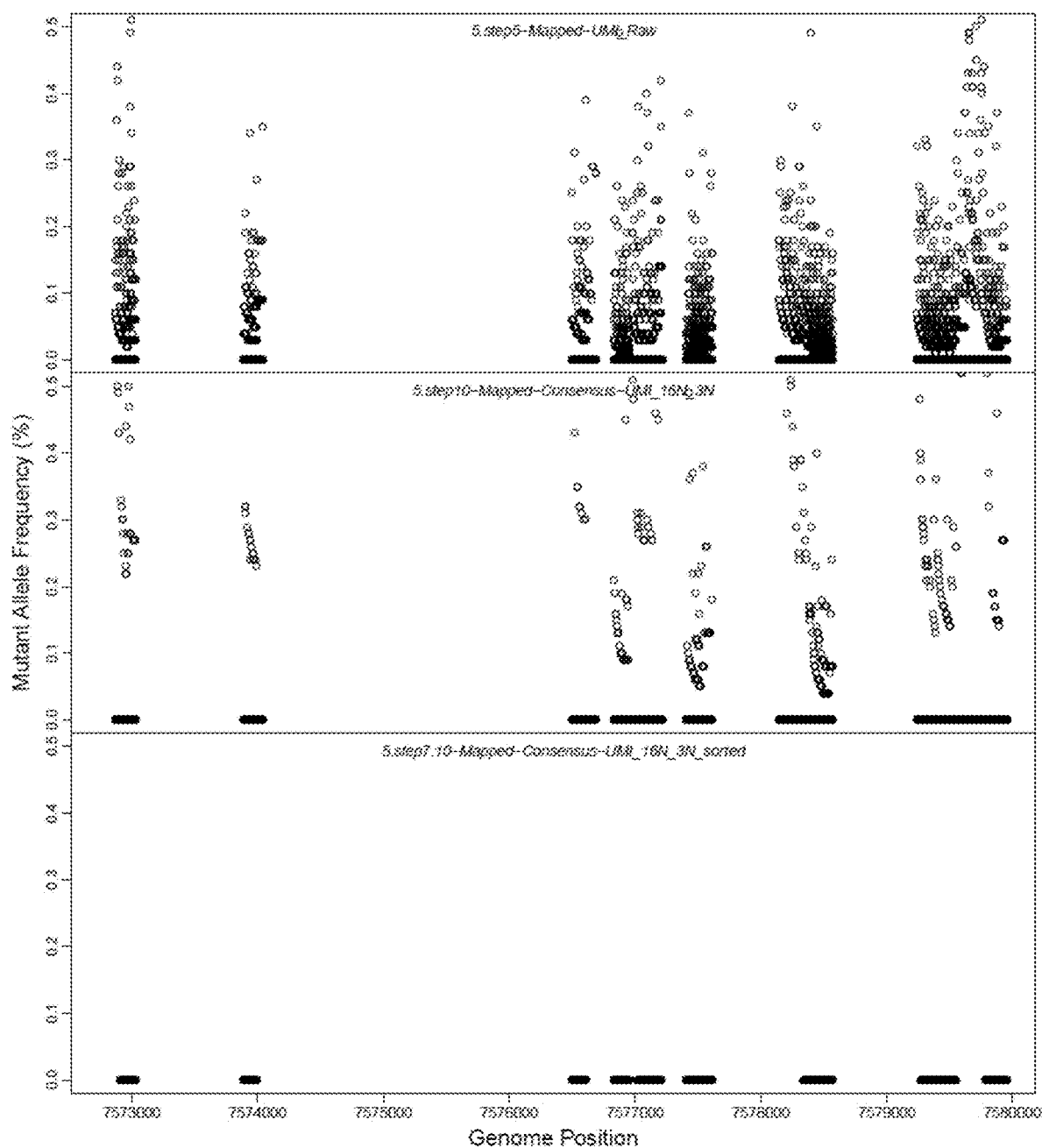
FIG. 8 shows one example of the reduction of the number of random base errors by TriSeq sequencing. The number and distribution of random bases errors on the human genome are shown after retrieving the raw reads (upper panel), finding consensus sequence from primary UMI clones (mid panel), and using TriSeq technology finding consensus sequences of both primary UMI clones and subclones (lower panel). One further layer of noise reduction, which is based on finding similar variant calls from forward and reverse primers, is not shown in this graph.

The amplified DNA library is purified and sequenced in an Illumina sequencing machine, such as Miseq or NextSeq. One example of TriSeq sequencing results is shown in FIG. 8. It shows the sequential reduction of random base errors by retrieving raw reads (upper panel), finding consensus sequence from primary UMI clones only (mid panel), and using TriSeq technology finding consensus sequences of both primary UMI clones and subclones (lower panel). FIG. 8 demonstrate one example of the effect of the reduction of random base errors by the technology of TriSeq sequencing method. One further layer of noise reduction, which is based on finding similar variant calls from forward and reverse primers, is not shown in this graph.

In some examples, the amplified DNA is amplified to a total of 0.5 to 3 micrograms. The DNA is purified by magnetic beads and the DNA concentration is measured by a spectrophotometer, such as a NanoDrop. In some examples, one microgram of the DNA is used in the downstream targeted multiplex PCR.

In some examples, one cycle of PCR is used to extend a panel of target-specific primers that are annealed to the amplified DNA fragments in the absence of dUTP. In some cases, a hot-start Taq polymerase is used. In some cases, a panel of forward target-specific primers, or a panel of reverse target-specific primers, a panel of forward and reverse target-specific primers, is used. Each target-specific primer of the panel may optionally contain a UMI region. In some cases, the UMI region comprises 2, or 3, or 4, or up to 16 random bases.

In some examples, the target-specific primers may comprise any appropriate plurality of primers or pairs of primers, such as 5 primers or pairs of primers or more (e.g., at least 5 primers or pairs of primers) of target-specific primers, such as 10 primers or pairs of primers or more (e.g., at least 10 primers or pairs of primers) of target-specific primers, between 5 and 100,000 primers or pairs of primers, between 5 and 1000 primers or pairs of primers, between 1,000 to 100,000 primers or pairs of primers, over 100,000 primers or pairs of primers of target-specific primers, etc., between 10 and 100,000 primers or pairs of primers, between 10 and 1000 primers or pairs of primers, etc. Although five or more primers or pairs of primers are specified and may be preferable, less than five pairs may be used (e.g., two or more primers or pairs of primers, three or more primers or pairs of primers, four or more primers or pairs of primers, five or more primers or pairs of primers, or six or more primers or pairs of primers, may be used). The target-specific primers may also comprise any appropriate plurality of primers plus any appropriate plurality of pairs of primers, such as 5 primers plus 5 pairs of primers.

In some examples, the types of primers that may be used may include unmodified oligonucleotides, modified oligonucleotides, peptide nucleic acid (PNA); modified primers may contain one or more than one 5-methyl deoxycytidine and/or 2,6-diaminopurine, dideoxyinosine, dideoxyuridine, and biotin labeled oligonucleotides. One and/or both primers can contain barcodes or other sequences that allow for identification; one and/or both primers can contain adapter sequences.

In some examples, the dU-containing template DNA and the single-stranded DNA fragments are reduced or eliminated, thereby the non-target templates, non-specific products, and the remaining primers of the panel are rendered un-amplifiable in the downstream PCR. In some cases, 10-20 units of UDG (MCLAB UDG-100) and 10-20 units of fpg (MCLAB FPG-100) are used to break the dU-containing template DNA. They are incubated with the DNA products at 37° ° C. for 30 minutes. Exonuclease I (NEB M0293L) is used simultaneously to reduce or eliminate the single-stranded DNA. In some cases, 20-40 units of Exonuclease I are used.

In the foregoing examples, one or more of the method steps is conducted in manual mode or in an automated mode or a combination thereof. In particular examples each of the method steps is carried out in automated mode. In some examples the foregoing methods further comprise at least one purification step. In particular examples a purification step is carried out only after the second PCR. In other particular examples a purification is carried out after the digestion step and an additional purification is carried out after the second PCR.

In some examples, the foregoing methods further comprise analyzing the nucleotide sequence of the resulting targeted DNA library. Such analyzing may comprise sequencing by traditional sequencing reactions, high throughput next generation sequencing, targeted multiplex array sequence detection, or any combination of two or more of the foregoing. In some examples, the foregoing methods further comprise deducing the consensus sequence from each UMI cluster of at least one target molecule in the sample. In other examples, the foregoing methods further comprise determining the abundance of at least one of the target nucleic acid sequences in the sample. In specific examples, the foregoing methods further comprise determining the low frequency allele(s) in a sample.

In some examples, the UMI-containing adapter additionally contains a universal prime site, which is used for the amplification of the target DNA molecules. The universal prime site is placed 5' to the UMI region, therefore the UMI is amplified into clones by PCR. This design allows low level of ctDNA (for example, 1-5 ng of cfDNA) to be amplified into levels of micrograms. Offering sufficient quantities of sample DNA through amplification improves the efficiencies of downstream DNA manipulations, as well as the sensitivity. In some examples, the universal primer may be an unmodified single-stranded DNA oligo, or a modified single-stranded DNA oligo. In some examples, the universal primer may contain dU bases replacing dT. Cleavage of the single-stranded DNA at sites of dU helps render the non-target DNA molecules un-amplifiable, as well as removing the unused universal primers before amplifying the target-specific molecules. In some examples, single-stranded DNA containing dU are cleaved by uracil DNA glycosylase (UDG) and apurinic/apyrimidinic endonuclease (e.g., human APE 1). In some examples, dU sites on single-stranded DNA are cleaved by using UDG and formamidopyrimidine [fapy]-DNA glycosylase (fpg).

In some examples, the panel contains a plurality of target-specific primers (e.g., >6, >10, >100, >1000, >10,000, etc.), each of the primer may additionally contain a region that serves as UMI and a region that serves as a second universal primer binding site. The panel may comprise reverse PCR primers, or forward PCR primers, or a combination of both forward and reverse primers. The panel is used to anneal onto the amplified DNA molecules, followed by a single round of extension in the absence of dUTP. Then template DNA molecules are broken, and single-stranded molecules are reduced or removed by a combination of Exonuclease I, UDG, and any one of APE I, fpg, Endo III, Endo VIII. In some examples, the resulting DNA molecules may be further amplified, during which the sample indexes and sequencing adapters are added. The final library may be used in downstream analysis, such as NGS sequencing.

In the methods described above, the amplification of the target is not limited by the length of the DNA fragments, and the requirement of the presence of two target-specific primer sites on the same DNA fragment is eliminated. Any targets, short and long and harboring one primer site, are amplified. The methods, apparatuses (e.g., systems) and compositions described herein may allow for amplifying and detecting a limited amount of starting material, such as cfDNA with high sensitivity. Further, the methods, apparatuses and compositions described herein may allow for amplifying and detecting structural change of DNA, such as fusion genes.

In general, the target nucleic acids may comprise DNA or RNA, for example, genomic DNA or cDNA, DNA purified from Formalin-Fixed, Paraffin-Embedded (FFPE) tissue samples (FFPE DNA), cell-free DNA (cfDNA) or circulating tumor DNA (ctDNA).

In some examples, the methods provided herein can be used for amplifying a plurality of DNA fragments and reducing the random base errors. The methods disclosed herein provide for optimized protocols such that DNA fragments are amplified, and random base errors are eliminated or reduced. Overall, the methods can relate to improved methods of nucleic acid library preparation.

In some examples, the amplification products described herein can be used to prepare libraries for next-generation sequencing. For example, the methods, compositions and apparatuses described herein may be useful for next-generation sequencing by the methods commercialized by Illumina, as described in U.S. Pat. No. 5,750,341 (Macevicz); U.S. Pat. No. 6,306,597 (Macevicz); and U.S. Pat. No. 5,969,119 (Macevicz).

Particular reference will now be made to specific aspects and figures of the disclosure. Such aspects are provided by way of example only. Numerous variations, changes, and substitutions will now occur to those skilled in the art without departing from the disclosure.

EXAMPLES

The following examples are given for the purpose of illustrating various examples of the invention and are not meant to limit the present invention in any fashion. The present examples, along with the methods described herein are presently representative of preferred examples, are exemplary, and are not intended as limitations on the scope of the invention. Changes therein and other uses which are encompassed within the spirit of the invention as defined by the scope of the claims will occur to those skilled in the art.

Example 1. Ligation of Adapter to DNA Fragments

Reagents:
 10× Ligation buffer (500 mM Tris-HCl, pH7.5, 100 mM MgCl$_2$, 5 mM ATP, 50 mM DTT)
 50 μM Single-stranded 5' adapter with UMI (Table 1, SEQ IDs NO: 1)
 50% PEG8000 in water
 T4 RNA Ligase 1 (NEB M0204L)
 RNase T (NEB M0265L)
End Repair Reaction:
 Add the following mix to make a 20 μl reaction:

| | |
|---|---|
| dH2O | 10 μl |
| DNA sample | 6 μl |
| 10X Ligation buffer | 2 μl |
| T4 PNK enzyme | 1 μl |
| RNase T | 1 μl |

Incubate at 25° C. for 40 minutes and 65° C. for 20 minutes.

Add 40 μl magnetic beads, incubate at room temperature for 15 minutes, wash twice with 70% ethanol, add 5 μl TE buffer to the pellet of magnetic beads and resuspend.
Adapter Ligation:
 Add the following mix to make a 20 μl ligation reaction:

| | |
|---|---|
| End-repair DNA (above) | 5 μl |
| 10X Ligation buffer | 2 μl |
| 10 mM ATP | 2 μl |
| 50 uM Adapter | 2 μl |
| DMSO | 4 μl |
| 50% PEG8000 | 4 μl |
| T4 RNA Ligase1 | 1 μl |

Incubate at 37°C for 2 hours.
Clean-Up:
 Add the following reagent:

| | |
|---|---|
| Ligation reaction (above) | 20 μl |
| RNase T | 1 μl |

Incubate at 25° ° C. for 60 minutes and 65° ° C. for 20 minutes.

Add 9 μl dH2O to the above reaction, then 60 μl magnetic beads, incubate at room temperature for 15 minutes, wash twice with 80% ethanol, add 10 μl TE buffer to the pellet of magnetic beads and resuspend.

Example 2. PCR Amplification with Universal Primer

Reagents:
 5×2$^{nd}$ PCR mix with 30% dUTP (Paragon Genomics) and Phusion U Hot Start DNA polymerase (F555L, Thermo Scientific)
 10 μM Universal primer for the first round of PCR (Table 1, SEQ IDs NO: 3)

Activation of the Hot-Start DNA Polymerase:
 Add the following mix to make a 30 μl reaction:

| | |
|---|---|
| dH2O | 18 μl |
| 5X 2$^{nd}$ PCR mix | 8 μl |
| 10 μM Universal primer | 4 μl |

Run the following thermal cycling protocol:

| | |
|---|---|
| Incubation | 98° C., 30 seconds |

First Round of PCR:
 Add the following to activated reaction mix (above):

| | |
|---|---|
| Ligated DNA (above) | 10 μl |
| Incubation | 65° C., 5 minutes |

Run 20 cycles:

| | |
|---|---|
| Denaturation | 98° C., 15 sec, 3° C./s |
| Annealing/Extension | 60° C., 75 sec, 2° C./s |
| Hold | 10° C., ∞ |

After PCR, add 80 μl magnetic beads, incubate at room temperature for 15 minutes, wash twice with 70% ethanol, elute DNA into 10 μl TE buffer.

Example 3. Annealing and Extension of a Panel of Target-Specific Primers

Reagents:
 5×mPCR mix (Paragon Genomics) with Phusion U Hot Start DNA polymerase (F555L, Thermo Scientific)
 30 nM Target-specific primer panel (Table 2, SEQ IDs NO: 6-89)
Annealing and Extension of a Panel:
 Add the following mix in a fresh tube to make a 20 μl reaction:

| | |
|---|---|
| 1 μg of DNA sample (above) | 10 μl |
| dH2O | 4 μl |
| 5X mPCR mix | 4 μl |
| 30 nM panel | 2 μl |

Run the following thermal cycling protocol:

| | |
|---|---|
| Initial incubation | 95° C., 10 min |
| Denaturation | 98° C., 15 sec, 3° C./s |
| Annealing/Extension | 60° C., 5 min, 0.4° C./s |
| Hold | 10° C., ∞ |

After PCR, add 2 μl STOP solution and 29 μl magnetic beads, incubate at room temperature for 15 minutes, wash twice with 80% ethanol, elute DNA into 10 μl TE buffer.

Example 4. Digestion and Amplification

Reagents:
 10×NEBuffer 4 (B7004S)
 UDG (MCLAB, UDG-100)
 fpg (MCLAB, FPG-100)
 Exonuclease I (NEB M0293L)

5× Ultra mPCR mix (Paragon Genomics)
10 µM Universal primers for the second round of PCR (Table 1, SEQ IDs NO: 4-5)

Digestion Reaction:

Add the following mix to a fresh tube to make a 30 µl reaction:

| | |
|---|---|
| dH2O | 12 µl |
| DNA sample (above) | 10 µl |
| 10X NEBuffer 4 | 3 µl |
| Exonuclease I | 2 µl |
| UDG | 1 µl |
| fpg | 2 µl |

Incubate at 37° ° C. for 30 minutes.

Immediately after digestion, add 2 µl STOP solution and 42 µl magnetic beads, incubate at room temperature for 15 minutes, wash twice with 80% ethanol, add 10 µl TE buffer to the pellet of magnetic beads and resuspend.

Second Round of PCR:

Add the following mix to the above DNA sample:

| | |
|---|---|
| DNA sample (above) | 10 µl |
| dH2O | 18 µl |
| 5X Ultra mPCR mix | 8 µl |
| 10 µM Universal primers | 4 µl |

Run the following thermal cycling protocol:
Run 24 cycles:

| Run 24 cycles: | |
|---|---|
| Denaturation | 98° C., 15 sec, 3° C./s |
| Annealing/Extension | 60° C., 75 sec, 2° C./s |
| Hold | 10° C., ∞ |

After PCR, add 40 µl magnetic beads, incubate at room temperature for 15 minutes, wash twice with 70% ethanol, elute DNA into 10 µl TE buffer.

DNA library was sequenced on an Illumina MiSeq sequencer at 2×150 bp read length.

It should be appreciated that all combinations of the foregoing concepts and additional concepts discussed in greater detail above (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

Section headings used herein are for organizational purposes only and are not to be construed as limiting the described subject matter in any way.

While various embodiments have been described and/or illustrated herein in the context of fully functional systems, one or more of these example embodiments may be distributed as a product in a variety of forms, regardless of the particular set of experiments used to actually reach the results.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

TABLES

TABLE 1

List of adapters and universal primers.

Single-stranded 5' adapter with UMI:
(SEQ ID NO: 1)
/5AmMC6/CCTACACGACGCTCTTCCGATCTNNN
NNNNNNNNNrNrNrNrN Single-stranded 5' adapter with
UMI and sample index:
(SEQ ID NO: 2)
/5AmMC6/AATGATACGGCGACCACCGAGAT
CTACAC-NNNNNNNN-ACACTCTTTCCCTAC
ACGACGCTCTTCCGATCTNNNNNNNNNNNNr
NrNrNrN Universal primer with Us for the
first round of PCR:
(SEQ ID NO: 3)
CCTACACGACGC/ideoxyU/CT/ideoxyU/
CCGA/ideoxyU/CT Universal primers for the second
round of PCR:
(SEQ ID NO: 4)
5'AATGATACGGCGACCACCGAGATCTACAC-
NNNNNNNN-ACACTCTTTCCCTACACGACGCT
CTTCCGATC*T
(SEQ ID NO: 5)
5'CAAGCAGAAGACGGCATACGAGAT-NNNNN
NNN-GTGACTGGAGTTCAGACGTGTGCTCTTC
CGATC*T

TABLE 2

List of a panel of target-specific primers.

| | |
|---|---|
| (SEQ ID NO: 6) | TTCAGACGTGTGCTCTTCCGATCTNNN CAGTCTACCTCCCGCCATA |
| (SEQ ID NO: 7) | TTCAGACGTGTGCTCTTCCGATCTNNN CAGACCAGCTTTCAAAAAGAAAATTGT |
| (SEQ ID NO: 8) | TTCAGACGTGTGCTCTTCCGATCTNNN CAAAGAAGAAACCACTGGATGGA |
| (SEQ ID NO: 9) | TTCAGACGTGTGCTCTTCCGATCTNNN CCCCCAGGGAGCACTAA |
| (SEQ ID NO: 10) | TTCAGACGTGTGCTCTTCCGATCTNNN ACGGAACAGCTTTGAGGTG |
| (SEQ ID NO: 11) | TTCAGACGTGTGCTCTTCCGATCTNNN GCCTCTTGCTTCTCTTTTCCT |
| (SEQ ID NO: 12) | TTCAGACGTGTGCTCTTCCGATCTNNN GACAGGTAGGACCTGATTTCCTTA |
| (SEQ ID NO: 13) | TTCAGACGTGTGCTCTTCCGATCTNNN TGACTGTACCACCATCCACT |
| (SEQ ID NO: 14) | TTCAGACGTGTGCTCTTCCGATCTNNN ATAGTGTGGTGGTGCCCTAT |
| (SEQ ID NO: 15) | TTCAGACGTGTGCTCTTCCGATCTNNN TCACTGAAGACCCAGGTCC |
| (SEQ ID NO: 16) | TTCAGACGTGTGCTCTTCCGATCTNNN TGAAAACAACGTTCTGGTAAGGAC |
| (SEQ ID NO: 17) | TTCAGACGTGTGCTCTTCCGATCTNNN CCTATGGAAACTGTGAGTGGATC |
| (SEQ ID NO: 18) | TTCAGACGTGTGCTCTTCCGATCTNNN TGGAAGTGTCTCATGCTGGA |
| (SEQ ID NO: 19) | TTCAGACGTGTGCTCTTCCGATCTNNN AAAAACTCATGTTCAAGACAGAAGG |
| (SEQ ID NO: 20) | TTCAGACGTGTGCTCTTCCGATCTNNN TCACTCATGTGATGTCATCTCTCC |
| (SEQ ID NO: 21) | TTCAGACGTGTGCTCTTCCGATCTNNN GAATGAGGCCTTGGAACTCAAG |
| (SEQ ID NO: 22) | TTCAGACGTGTGCTCTTCCGATCTNNN TGTATATACTTACTTCTCCCCCTCCT |
| (SEQ ID NO: 23) | TTCAGACGTGTGCTCTTCCGATCTNNN GGTTCTATGACTTTGCCTGATACAG |
| (SEQ ID NO: 24) | TTCAGACGTGTGCTCTTCCGATCTNNN GAAAATTGTTAAAGAGAGCATGAAAAT GGT |
| (SEQ ID NO: 25) | TTCAGACGTGTGCTCTTCCGATCTNNN CCTGGTTGTAGCTAACTAACTTCAG |
| (SEQ ID NO: 26) | TTCAGACGTGTGCTCTTCCGATCTNNN CTTTTATCACCTTTCCTTGCCTCTT |
| (SEQ ID NO: 27) | TTCAGACGTGTGCTCTTCCGATCTNNN GCAGTTATGCCTCAGATTCACTTT |
| (SEQ ID NO: 28) | TTCAGACGTGTGCTCTTCCGATCTNNN GGAAGAGAATCTCCGCAAGAAAG |
| (SEQ ID NO: 29) | TTCAGACGTGTGCTCTTCCGATCTNNN GTGGTAATCTACTGGGACGGA |
| (SEQ ID NO: 30) | TTCAGACGTGTGCTCTTCCGATCTNNN GGAGTAGATGGAGCCTGGTT |
| (SEQ ID NO: 31) | TTCAGACGTGTGCTCTTCCGATCTNNN CCATCATCACACTGGAAGACTC |
| (SEQ ID NO: 32) | TTCAGACGTGTGCTCTTCCGATCTNNN ATGGGCGGCATGAACCG |
| (SEQ ID NO: 33) | TTCAGACGTGTGCTCTTCCGATCTNNN CCTCATCTTGGGCCTGTGTTA |
| (SEQ ID NO: 34) | TTCAGACGTGTGCTCTTCCGATCTNNN AAGGAAATTTGCGTGTGGAGT |
| (SEQ ID NO: 35) | TTCAGACGTGTGCTCTTCCGATCTNNN CACTGATTGCTCTTAGGTCTGG |
| (SEQ ID NO: 36) | TTCAGACGTGTGCTCTTCCGATCTNNN CGCTGCTCAGATAGCGATG |
| (SEQ ID NO: 37) | TTCAGACGTGTGCTCTTCCGATCTNNN CGCCATGGCCATCTACAAG |
| (SEQ ID NO: 38) | TTCAGACGTGTGCTCTTCCGATCTNNN CCTGCCCTCAACAAGATGTTTT |
| (SEQ ID NO: 39) | TTCAGACGTGTGCTCTTCCGATCTNNN CCCTGACTTTCAACTCTGTCTC |
| (SEQ ID NO: 40) | TTCAGACGTGTGCTCTTCCGATCTNNN TGACTTGCACGGTCAGTTG |
| (SEQ ID NO: 41) | TTCAGACGTGTGCTCTTCCGATCTNNN GTCCCTTCCCAGAAAACCTAC |
| (SEQ ID NO: 42) | TTCAGACGTGTGCTCTTCCGATCTNNN CAGATGAAGCTCCCAGAATGC |

TABLE 2-continued

List of a panel of target-specific primers.

| | |
|---|---|
| (SEQ ID NO: 43) | TTCAGACGTGTGCTCTTCCGATCTNNN GTCCCCGGACGATATTGAAC |
| (SEQ ID NO: 44) | TTCAGACGTGTGCTCTTCCGATCTNNN TGGTCCTCTGACTGCTCTTTT |
| (SEQ ID NO: 45) | TTCAGACGTGTGCTCTTCCGATCTNNN CCCCTAGCAGAGACCTGTG |
| (SEQ ID NO: 46) | TTCAGACGTGTGCTCTTCCGATCTNNN AGCCGCAGTCAGATCCTAG |
| (SEQ ID NO: 47) | TTCAGACGTGTGCTCTTCCGATCTNNN CCACTTTTCCTCTTGCAGCAG |
| (SEQ ID NO: 48) | TTCAGACGTGTGCTCTTCCGATCTNNN GTTCAAAGACCCAAAACCCAAAATG |
| (SEQ ID NO: 49) | TTCAGACGTGTGCTCTTCCGATCTNNN TGGAGAATGTCAGTCTGAGTCAG |
| (SEQ ID NO: 50) | TTCAGACGTGTGCTCTTCCGATCTNNN CCTATGGCTTTCCAACCTAGGAA |
| (SEQ ID NO: 51) | TTCAGACGTGTGCTCTTCCGATCTNNN GGTCACTCACCTGGAGTGAG |
| (SEQ ID NO: 52) | TTCAGACGTGTGCTCTTCCGATCTNNN AGGCTAAGCTATGATGTTCCTTAGATT |
| (SEQ ID NO: 53) | TTCAGACGTGTGCTCTTCCGATCTNNN AACTTACAATATTTTCAACTTACGACG AGT |
| (SEQ ID NO: 54) | TTCAGACGTGTGCTCTTCCGATCTNNN GCAAAGTCATAGAACCATTTTCATGCT |
| (SEQ ID NO: 55) | TTCAGACGTGTGCTCTTCCGATCTNNN GGAAACTTTCCACTTGATAAGAGGTC |
| (SEQ ID NO: 56) | TTCAGACGTGTGCTCTTCCGATCTNNN TGAAGGGTGAAATATTCTCCATCCA |
| (SEQ ID NO: 57) | TTCAGACGTGTGCTCTTCCGATCTNNN TAAAAGTGAATCTGAGGCATAACTGC |
| (SEQ ID NO: 58) | TTCAGACGTGTGCTCTTCCGATCTNNN TGCTTACCTCGCTTAGTGCT |
| (SEQ ID NO: 59) | TTCAGACGTGTGCTCTTCCGATCTNNN GCACAAACACGCACCTCAA |
| (SEQ ID NO: 60) | TTCAGACGTGTGCTCTTCCGATCTNNN GAGGTGGATGGGTAGTAGTATGG |
| (SEQ ID NO: 61) | TTCAGACGTGTGCTCTTCCGATCTNNN GGAAGAAATCGGTAAGAGGTGG |
| (SEQ ID NO: 62) | TTCAGACGTGTGCTCTTCCGATCTNNN CCAGTGTGATGATGGTGAGGAT |
| (SEQ ID NO: 63) | TTCAGACGTGTGCTCTTCCGATCTNNN CCACTGACAACCACCCTTAAC |
| (SEQ ID NO: 64) | TTCAGACGTGTGCTCTTCCGATCTNNN ATAGGGCACCACCACACTAT |
| (SEQ ID NO: 65) | TTCAGACGTGTGCTCTTCCGATCTNNN TTCCACTCGGATAAGATGCTGA |
| (SEQ ID NO: 66) | TTCAGACGTGTGCTCTTCCGATCTNNN GCAACCAGCCCTGTCGT |
| (SEQ ID NO: 67) | TTCAGACGTGTGCTCTTCCGATCTNNN CTCACAACCTCCGTCATGT |
| (SEQ ID NO: 68) | TTCAGACGTGTGCTCTTCCGATCTNNN GGGTGTGGAATCAACCCAC |
| (SEQ ID NO: 69) | TTCAGACGTGTGCTCTTCCGATCTNNN GGTGAAGAGGAATCCCAAAGTTC |
| (SEQ ID NO: 70) | TTCAGACGTGTGCTCTTCCGATCTNNN CATTGAAGTCTCATGGAAGCCA |
| (SEQ ID NO: 71) | TTCAGACGTGTGCTCTTCCGATCTNNN CAGACGGAAACCGTAGCT |
| (SEQ ID NO: 72) | TTCAGACGTGTGCTCTTCCGATCTNNN AGGGACAGAAGATGACAGGG |
| (SEQ ID NO: 73) | TTCAGACGTGTGCTCTTCCGATCTNNN CTGGACCTGGGTCTTCAGT |
| (SEQ ID NO: 74) | TTCAGACGTGTGCTCTTCCGATCTNNN AGCCCAACCCTTGTCCTTA |
| (SEQ ID NO: 75) | TTCAGACGTGTGCTCTTCCGATCTNNN TGGAATTTTCGCTTCCCACAG |
| (SEQ ID NO: 76) | TTCAGACGTGTGCTCTTCCGATCTNNN ACAGTTTCCATAGGTCTGAAAATGTTT |
| (SEQ ID NO: 77) | TTCAGACGTGTGCTCTTCCGATCTNNN GACCCAAAACCCAAAATGGC |
| (SEQ ID NO: 78) | TTCAGACGTGTGCTCTTCCGATCTNNN CTCATTCAGCTCTCGGAACATC |
| (SEQ ID NO: 79) | TTCAGACGTGTGCTCTTCCGATCTNNN GTTAGACTGGAAACTTTCCACTTGA |
| (SEQ ID NO: 80) | TTCAGACGTGTGCTCTTCCGATCTNNN GGGAGAGGAGCTGGTGTT |
| (SEQ ID NO: 81) | TTCAGACGTGTGCTCTTCCGATCTNNN CAGCTCGTGGTGAGGCT |
| (SEQ ID NO: 82) | TTCAGACGTGTGCTCTTCCGATCTNNN CCGTCCCAGTAGATTACCACTA |
| (SEQ ID NO: 83) | TTCAGACGTGTGCTCTTCCGATCTNNN CACAGCAGGCCAGTGTG |
| (SEQ ID NO: 84) | TTCAGACGTGTGCTCTTCCGATCTNNN CCCATGCAGGAACTGTTACAC |
| (SEQ ID NO: 85) | TTCAGACGTGTGCTCTTCCGATCTNNN AGTTGCAAACCAGACCTCAG |
| (SEQ ID NO: 86) | TTCAGACGTGTGCTCTTCCGATCTNNN TAGCTGCCCTGGTAGGTTT |
| (SEQ ID NO: 87) | TTCAGACGTGTGCTCTTCCGATCTNNN GGCATTCTGGGAGCTTCAT |
| (SEQ ID NO: 88) | TTCAGACGTGTGCTCTTCCGATCTNNN ATCAAATCATCCATTGCTTGGGA |
| (SEQ ID NO: 89) | TTCAGACGTGTGCTCTTCCGATCTNNN CCTGCCCTTCCAATGGATC |

The invention claimed is:

1. A method of reducing base errors in sequencing double-stranded DNA targets, wherein sequences of the double-stranded DNA targets are divided into a forward group of sequences amplified from a plurality of forward target-specific primers and a reverse group of sequences amplified from a plurality of reverse target-specific primers; wherein within both the forward group and the reverse group, respectively, a primary Unique Molecular Identifier (UMI) clone of a DNA target is subdivided into UMI subclones along the course of DNA amplifications; wherein after sequencing, base errors are reduced by finding a consensus sequence in each UMI subclone, then in each primary UMI clone, and then variant calls are confirmed between the consensus sequences obtained from the forward group and the consensus sequences obtained from the reverse group, the method comprising:

forming the primary UMI clones from double-stranded DNA molecules by:
  ligating the 3' end of a single-stranded adapter to the 5' end of both the sense and antisense strands of each of a plurality of double-stranded DNA molecules to form adapter-DNA complexes, wherein the single-stranded adapter comprises, from 5' to 3' end, a first universal primer binding site for PCR amplification and a UMI comprising a stretch of single-stranded DNA followed by a stretch of RNA, the entire UMI comprising 8 or more degenerate or semi-degenerate bases, and
  amplifying the adapter-DNA complexes in the presence of dUTP with a first universal primer, resulting in each strand of the DNA molecule producing a primary clone of itself;

subdividing each primary UMI clone into UMI subclones comprising:
  annealing and extending a plurality of target-specific forward and reverse primers to the primary UMI clones in the absence of dUTP, wherein each of the target-specific forward and reverse primers comprises a target-specific region, a UMI and a second universal primer binding site for PCR amplification, resulting in each primary UMI clone being subdivided into multiple UMI subclones defined by the UMIs on the target-specific forward and reverse primers on one side of the resulting molecules, while each primary UMI clone is still identifiable by the UMI from the adapter on the other side of the resulting molecules, and
  enzymatically creating nicks and breaks on the DNA at sites of dU bases and removing single-stranded DNA from the 3' ends, and
  amplifying the resulting products using a pair of second universal primers;

sequencing the resulting products; and removing base errors and finding variants after sequencing, comprising:
  sorting the sequences into a forward group of sequences and a reverse group of sequences by the forward and reverse target-specific primers, respectively, and
  within each of the forward group of sequences and the reverse group of sequences, respectively, sorting sequences into primary UMI clones by UMIs on the adapters on one side of the molecules, then sorting each primary clone into UMI subclones by the UMIs on the forward and reverse target-specific primers on the other side of the molecules, and
  within each of the forward group of sequences and the reverse group of sequences, respectively, deducing a consensus sequence from each UMI subclone, then deducing a consensus sequence in each primary UMI clone from the consensus sequences obtained from the UMI subclones within each primary UMI clone,
  finding variants, respectively, from all the consensus sequences obtained from the forward group of sequences and all the consensus sequences obtained from the reverse group of sequences; and
  confirming the existence of these variants at the same positions on both the sequence derived from the target-specific forward primers and the sequence derived from the target-specific reverse primers.

2. The method of claim 1, wherein ligating the adapter further comprises blunting ends and phosphorylating the 5' ends of the DNA molecules.

3. The method of claim 1, wherein the single-stranded-adapter comprises from the 5' end to the 3' end: a stretch of single-stranded DNA forming the first universal primer binding site, a stretch of single-stranded DNA comprising degenerated DNA bases forming the first part of the UMI, and a stretch of RNA comprising degenerated RNA bases forming the second part of the UMI.

4. The method of claim 3, wherein the stretch of RNA of the single-stranded adapter comprises 3 to 8 degenerated ribonucleotides (rNs).

5. The method of claim 1, wherein the single-stranded-adapter is ligated to the 5' end of the DNA molecules by T4 RNA Ligase 1.

6. The method of claim 1, wherein the degenerate or semi-degenerate bases in the UMI of the adapter have between 8 and 20 random bases.

7. The method of claim 1, wherein amplifying the adapter-DNA complexes comprises amplifying with one universal primer by PCR or linear amplification in the presence of dUTP.

8. The method of claim 1, wherein the universal primers have one or multiple dU bases replacing dT bases.

9. The method of claim 1, wherein the adapter-DNA complexes are amplified in the presence of between 20% dUTP to 60% dUTP.

10. The method of claim 1, wherein a dU-tolerant DNA polymerase or a combination of dU-tolerant DNA polymerases is used in both amplifying the adapter-ligated DNA fragments and the primer extension reaction involving a plurality of target-specific forward and reverse primers.

11. The method of claim 1, wherein the number of the plurality of target-specific primers is 2-100,000.

12. The method of claim 1, wherein enzymatically creating nicks and breaks on the DNA at sites of dU bases comprises creating nicks in double stranded DNA and breaks in single-stranded DNA at the sites of dU bases by using uracil DNA glycosylase (UDG) and apurinic/apyrimidinic endonuclease.

13. The method of claim 12, wherein using uracil DNA glycosylase (UDG) and apurinic/apyrimidinic endonuclease comprises using any one or a combination of: APE 1, formamidopyrimidine [fapy]-DNA glycosylase (fpg), Endonuclease III, and Endonuclease VIII.

14. The method of claim 1, wherein removing the single-stranded DNA from the 3' ends comprises treating the single-stranded DNA regions and/or fragments with a 3'-5' exonuclease.

15. The method of claim 1, wherein amplifying the resulting products includes adding sample barcodes.

16. The method of claim 1, further comprising hybridization capture after amplifying the adapter-DNA complexes.

17. The method of claim 1, wherein deducing a consensus sequence in each primary UMI clone further comprises calculating mutation frequency based on the number of clones of a specific mutation.

18. A method of reducing base errors in sequencing double-stranded DNA targets, wherein the sequences are divided into a forward group of sequences amplified from a plurality of forward target-specific primers and a reverse group of sequences amplified from a plurality of reverse target-specific primers; wherein within both the forward and the reverse group, respectively, a primary Unique Molecular Identifier (UMI) clone of a DNA target is subdivided into UMI subclones along the course of DNA amplifications; wherein base errors are reduced by finding a consensus sequence in each UMI subclone, then in each UMI primary clone, and then variant calls are confirmed between the consensus sequences obtained from the forward group and the consensus sequences obtained from the reverse group, the method comprising:

forming primary UMI clones from double-stranded DNA molecules by:
  ligating the 3' end of a single-stranded adapter to the 5' end of both the sense and antisense strands of each of a plurality of double-stranded DNA molecules, wherein the single-stranded adapter comprises, from 5' to 3' end, a sample index, a first universal primer binding site for PCR amplification, and a UMI comprising a stretch of single-stranded DNA followed by a stretch of RNA, the entire UMI comprising 8 or more degenerate or semi-degenerate bases, and
  amplifying the adapter-DNA complexes in the presence of dUTP with a first universal primer, resulting in each strand of the DNA molecules producing a primary clone of itself, and
  pooling samples and enriching the DNA molecules by hybridization capture, comprising pooling together the amplified plurality of DNA molecules from multiple samples, followed by hybridization and capturing with a plurality of target-specific oligos, wherein each of the target-specific oligos is tagged with a biotin moiety for capturing with streptavidin-coupled magnetic beads;
subdividing each primary UMI clone into UMI subclones by:
  annealing and extending a plurality of target-specific forward and reverse primers to the primary UMI clones in the absence of dUTP, wherein each of the target-specific primers comprises a target-specific region, a UMI and a second universal primer binding site for PCR amplification, resulting in each primary UMI clone being subdivided into multiple UMI subclones defined by the UMIs on the forward and reverse target-specific primers on one side of the resulting molecules, while each primary UMI clone is still identifiable by the UMI from the adapter on the other side of the resulting molecules, and
  enzymatically creating nicks and breaks on the DNA at sites of dU bases and removing single-stranded DNA from the 3' ends, and
  amplifying the resulting products using a pair of second universal primers;
sequencing the resulting products; and
removing base errors after sequencing, comprising:
  sorting the sequences into a forward group of sequences and a reverse group of sequences by the forward and reverse target specific primers, respectively, and
  within each of the forward and the reverse group of sequences, respectively, sorting sequences into primary UMI clones by UMIs on the adapters on one side of the molecules, then sorting each primary UMI clone into UMI subclones by the UMIs on the forward and reverse target-specific primers on the other side of the molecules, and
  within each of the forward and the reverse group of sequences, respectively, deducing a consensus sequence from each UMI subclone, then deducing a consensus sequence in each primary UMI clone from the consensus sequences obtained from the subclones within each primary UMI clone, and
  finding variants, respectively, from all the consensus sequences obtained from the forward group of sequences and all the consensus sequences obtained from the reverse group of sequences; confirming the existence of these variants at the same positions on both the sequence derived the target-specific forward primers and the sequence derived from the target-specific reverse primers.

\* \* \* \* \*